US012569481B2

(12) United States Patent
Pulley et al.

(10) Patent No.: US 12,569,481 B2
(45) Date of Patent: Mar. 10, 2026

(54) METHODS OF TREATMENT FOR GASTROINTESTINAL MOTILITY DISORDERS

(71) Applicant: Vanderbilt University, Nashville, TN (US)

(72) Inventors: Jill M. Pulley, Nashville, TN (US); Rebecca N. Jerome, Nashville, TN (US); Dawn B. Beaulieu, Nashville, TN (US); Jana K. Shirey-Rice, Brentwood, TN (US); Nicole M. Zaleski, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 727 days.

(21) Appl. No.: 18/001,180

(22) PCT Filed: Jun. 11, 2021

(86) PCT No.: PCT/US2021/037086
§ 371 (c)(1),
(2) Date: Dec. 8, 2022

(87) PCT Pub. No.: WO2021/252951
PCT Pub. Date: Dec. 16, 2021

(65) Prior Publication Data

US 2023/0255958 A1 Aug. 17, 2023

Related U.S. Application Data

(60) Provisional application No. 63/038,326, filed on Jun. 12, 2020.

(51) Int. Cl.
*A61K 31/495* (2006.01)
*A61K 45/06* (2006.01)
*A61P 1/12* (2006.01)

(52) U.S. Cl.
CPC ............ *A61K 31/495* (2013.01); *A61K 45/06* (2013.01); *A61P 1/12* (2018.01)

(58) Field of Classification Search
CPC .................................................. A61K 31/495
USPC .................................................. 514/252.12
See application file for complete search history.

(56) References Cited

U.S. PATENT DOCUMENTS

| | | | |
|---|---|---|---|
| 4,567,264 | A | 1/1986 | Kluge et al. |
| 5,506,229 | A | 4/1996 | Dow et al. |
| 5,906,988 | A | 5/1999 | Dow et al. |
| 5,962,477 | A | 10/1999 | Mak |
| 6,190,691 | B1 | 2/2001 | Mak |
| 6,303,607 | B1 | 10/2001 | Wolff et al. |
| 6,369,062 | B1 | 4/2002 | Wolff et al. |
| 6,479,496 | B1 | 11/2002 | Wolff |
| 6,503,911 | B2 | 1/2003 | Wolff et al. |
| 6,525,057 | B2 | 2/2003 | Wolff et al. |
| 6,562,826 | B1 | 5/2003 | Wolff |
| 6,617,328 | B2 | 9/2003 | Wolff et al. |
| 6,620,814 | B2 | 9/2003 | Wolff et al. |
| 6,852,724 | B2 | 2/2005 | Wolff |
| 6,864,258 | B2 | 3/2005 | Wolff |
| 7,510,710 | B2 | 3/2009 | Newell et al. |
| 7,582,629 | B2 | 9/2009 | Boström et al. |
| 7,674,820 | B2 | 3/2010 | Fedida et al. |
| 7,801,686 | B2 | 9/2010 | Hyde et al. |
| 7,816,383 | B1 | 10/2010 | Bradford et al. |
| 7,871,643 | B2 | 1/2011 | Lizio et al. |
| 7,974,787 | B2 | 7/2011 | Hyde et al. |
| 8,071,645 | B2 | 12/2011 | Newell et al. |
| 8,173,625 | B2 | 5/2012 | Brittain et al. |
| 8,202,895 | B2 | 6/2012 | Brüggemeier et al. |
| 8,236,787 | B2 | 8/2012 | Piccariello et al. |
| 8,420,825 | B2 | 4/2013 | Vakalopoulos et al. |
| 8,606,592 | B2 | 12/2013 | Hyde et al. |
| 8,615,407 | B2 | 12/2013 | Hyde et al. |
| 8,682,687 | B2 | 3/2014 | Hyde et al. |
| 8,930,208 | B2 | 1/2015 | Hyde et al. |
| 8,987,292 | B2 | 3/2015 | Safdi et al. |
| 9,026,369 | B2 | 5/2015 | Hyde et al. |
| 9,034,855 | B2 | 5/2015 | Fürstner et al. |
| 9,064,036 | B2 | 6/2015 | Hyde et al. |
| 9,180,120 | B2 | 11/2015 | Fürstner et al. |
| 9,449,150 | B2 | 9/2016 | Hyde et al. |
| 9,481,672 | B2 | 11/2016 | Fürstner et al. |
| 9,604,996 | B2 | 3/2017 | Härter et al. |
| 9,624,198 | B2 | 4/2017 | Becker-Pelster et al. |
| 9,624,199 | B2 | 4/2017 | Becker-Pelster et al. |
| 9,643,956 | B2 | 5/2017 | Andres et al. |

(Continued)

FOREIGN PATENT DOCUMENTS

| | | |
|---|---|---|
| CA | 2944614 A1 | 10/2015 |
| CA | 2944617 A1 | 10/2015 |

(Continued)

OTHER PUBLICATIONS

Adzhubei I, et al. Predicting functional effect of human missense mutations using PolyPhen-2. Curr Protoc Hum Genet Editor Board Jonathan Haines Al. Jan. 2013;Chapter 7:Unit7.20 (52 pages).

(Continued)

*Primary Examiner* — Raymond J Henley, III

(74) *Attorney, Agent, or Firm* — Michael Best & Friedrich LLP

(57) ABSTRACT

Disclosed herein are methods for treating or reducing symptoms of a gastrointestinal motility disorder in a subject. The methods include administering to the subject a therapeutically effective amount of a sodium channel blocker compound.

20 Claims, 5 Drawing Sheets

(56) References Cited

U.S. PATENT DOCUMENTS

| | | | |
|---|---|---|---|
| 9,668,977 | B2 | 6/2017 | Schattka et al. |
| 9,695,131 | B2 | 7/2017 | Fürstner et al. |
| 9,751,843 | B2 | 9/2017 | Fürstner et al. |
| 9,771,352 | B2 | 9/2017 | Schmeck et al. |
| 9,775,815 | B2 | 10/2017 | Schattka et al. |
| 9,862,711 | B2 | 1/2018 | Bellenie et al. |
| 9,944,621 | B2 | 4/2018 | Becker-pelster et al. |
| 10,238,712 | B2 | 3/2019 | Shailubhai |
| 2005/0020682 | A1 | 1/2005 | Newell et al. |
| 2005/0119315 | A1 | 6/2005 | Fedida et al. |
| 2006/0140953 | A1 | 6/2006 | Newell et al. |
| 2006/0241134 | A1 | 10/2006 | Buhr et al. |
| 2006/0269605 | A1 | 11/2006 | Lizio et al. |
| 2007/0042045 | A1 | 2/2007 | Lizio et al. |
| 2008/0152719 | A1 | 6/2008 | Petereit et al. |
| 2008/0193414 | A1 | 8/2008 | Proudfoot et al. |
| 2008/0193522 | A1 | 8/2008 | Meier et al. |
| 2008/0194494 | A1 | 8/2008 | Martinez et al. |
| 2009/0042819 | A1 | 2/2009 | Ellis et al. |
| 2009/0054319 | A1 | 2/2009 | Talley et al. |
| 2009/0131342 | A1 | 5/2009 | Ellis |
| 2009/0203653 | A1 | 8/2009 | Garvey |
| 2009/0267758 | A1 | 10/2009 | Hyde et al. |
| 2009/0269329 | A1 | 10/2009 | Hyde et al. |
| 2009/0270687 | A1 | 10/2009 | Hyde et al. |
| 2009/0270688 | A1 | 10/2009 | Hyde et al. |
| 2009/0270693 | A1 | 10/2009 | Hyde et al. |
| 2009/0270694 | A1 | 10/2009 | Hyde et al. |
| 2009/0271008 | A1 | 10/2009 | Hyde et al. |
| 2009/0271009 | A1 | 10/2009 | Hyde et al. |
| 2009/0271122 | A1 | 10/2009 | Hyde et al. |
| 2009/0271217 | A1 | 10/2009 | Hyde et al. |
| 2009/0271347 | A1 | 10/2009 | Hyde et al. |
| 2009/0271375 | A1 | 10/2009 | Hyde et al. |
| 2009/0292676 | A1 | 11/2009 | Leuthardt et al. |
| 2009/0312595 | A1 | 12/2009 | Leuthardt et al. |
| 2009/0312668 | A1 | 12/2009 | Euthardt et al. |
| 2009/0319301 | A1 | 12/2009 | Hyde et al. |
| 2010/0004762 | A1 | 1/2010 | Leuthardt et al. |
| 2010/0015583 | A1 | 1/2010 | Leuthardt et al. |
| 2010/0017001 | A1 | 1/2010 | Leuthardt et al. |
| 2010/0022820 | A1 | 1/2010 | Leuthardt et al. |
| 2010/0030089 | A1 | 2/2010 | Hyde et al. |
| 2010/0041958 | A1 | 2/2010 | Leuthardt et al. |
| 2010/0041964 | A1 | 2/2010 | Hyde et al. |
| 2010/0042578 | A1 | 2/2010 | Leuthardt et al. |
| 2010/0048520 | A1 | 2/2010 | Safdi et al. |
| 2010/0063368 | A1 | 3/2010 | Leuthardt et al. |
| 2010/0069724 | A1 | 3/2010 | Leuthardt et al. |
| 2010/0076249 | A1 | 3/2010 | Leuthardt et al. |
| 2010/0081860 | A1 | 4/2010 | Leuthardt et al. |
| 2010/0081861 | A1 | 4/2010 | Leuthardt et al. |
| 2010/0100036 | A1 | 4/2010 | Leuthardt et al. |
| 2010/0120694 | A1 | 5/2010 | Shailubhai et al. |
| 2010/0125561 | A1 | 5/2010 | Leuthardt et al. |
| 2010/0130811 | A1 | 5/2010 | Leuthardt et al. |
| 2010/0152118 | A1 | 6/2010 | Shailubhai |
| 2010/0247639 | A1 | 9/2010 | Ravishankar et al. |
| 2010/0255092 | A1 | 10/2010 | Ravishankar et al. |
| 2010/0261771 | A1 | 10/2010 | Brüggemeier et al. |
| 2010/0280332 | A1 | 11/2010 | Hyde et al. |
| 2010/0291202 | A1 | 11/2010 | Ravishankar et al. |
| 2011/0054017 | A1 | 3/2011 | Lampe et al. |
| 2011/0136871 | A1 | 6/2011 | Hübsch et al. |
| 2011/0207698 | A1 | 8/2011 | Meibom et al. |
| 2011/0245308 | A1 | 10/2011 | Brüggemeier et al. |
| 2011/0300218 | A1 | 12/2011 | Athukuri et al. |
| 2012/0053218 | A1 | 3/2012 | Brüggemeier et al. |
| 2012/0208852 | A1 | 8/2012 | Fürstner et al. |
| 2012/0283229 | A1 | 11/2012 | Glick |
| 2012/0329780 | A1 | 12/2012 | Thormann et al. |
| 2012/0329785 | A1 | 12/2012 | Thormann et al. |
| 2013/0022676 | A1 | 1/2013 | Mullen et al. |
| 2014/0050694 | A1 | 2/2014 | Mezrich et al. |
| 2014/0187470 | A1 | 7/2014 | Jacob et al. |
| 2014/0271923 | A1 | 9/2014 | Reid |
| 2014/0287002 | A1 | 9/2014 | Shailubhai |
| 2014/0328884 | A1 | 11/2014 | Reyes et al. |
| 2015/0273013 | A1 | 10/2015 | Shailubhai |
| 2015/0306230 | A1 | 10/2015 | Combs et al. |
| 2016/0279263 | A1 | 9/2016 | Putnam et al. |
| 2016/0367623 | A1 | 12/2016 | Shailubhai |
| 2017/0022171 | A1 | 1/2017 | Beck et al. |
| 2017/0121315 | A1 | 5/2017 | Beck et al. |
| 2017/0231560 | A1 | 8/2017 | Hyde et al. |
| 2017/0260140 | A1 | 9/2017 | Beck et al. |
| 2017/0319698 | A1 | 11/2017 | Vergnault et al. |
| 2017/0320854 | A1 | 11/2017 | Collin et al. |
| 2018/0018328 | A1 | 1/2018 | Hyde et al. |
| 2018/0036300 | A1 | 2/2018 | Beck et al. |
| 2018/0064767 | A1 | 3/2018 | Mckenna |
| 2018/0065981 | A1 | 3/2018 | Härter et al. |

FOREIGN PATENT DOCUMENTS

| | | | |
|---|---|---|---|
| CN | 1863515 | A | 11/2006 |
| CN | 101137630 | A | 3/2008 |
| DE | 102007061766 | A1 | 6/2009 |
| DE | 102008052013 | A1 | 4/2010 |
| DE | 102010030187 | A1 | 12/2011 |
| EP | 2720683 | B1 | 8/2016 |
| EP | 2956455 | B1 | 5/2017 |
| EP | 3134395 | B1 | 1/2018 |
| EP | 3296298 | A1 | 3/2018 |
| IN | 101098861 | A | 1/2008 |
| WO | 1995027510 | A1 | 10/1995 |
| WO | 2004058224 | A1 | 7/2004 |
| WO | 2004058226 | A1 | 7/2004 |
| WO | 2006010457 | A2 | 2/2006 |
| WO | 2006073364 | A1 | 7/2006 |
| WO | 2006073365 | A1 | 7/2006 |
| WO | 2006073366 | A1 | 7/2006 |
| WO | 2006102674 | A2 | 9/2006 |
| WO | 2006102964 | A2 | 10/2006 |
| WO | 2006120160 | A1 | 11/2006 |
| WO | 2006121861 | A2 | 11/2006 |
| WO | 2006122186 | A2 | 11/2006 |
| WO | 2006124713 | A2 | 11/2006 |
| WO | 2007016677 | A2 | 2/2007 |
| WO | 2007059311 | A2 | 5/2007 |
| WO | 2007084450 | A2 | 7/2007 |
| WO | 2007103448 | A2 | 9/2007 |
| WO | 2007123949 | A2 | 11/2007 |
| WO | 2007134862 | A1 | 11/2007 |
| WO | 2008031500 | A1 | 3/2008 |
| WO | 2008031501 | A2 | 3/2008 |
| WO | 2008039829 | A2 | 4/2008 |
| WO | 2008100977 | A2 | 8/2008 |
| WO | 2008130616 | A2 | 10/2008 |
| WO | 2008151257 | A2 | 12/2008 |
| WO | 2009033561 | A1 | 3/2009 |
| WO | 2009036811 | A1 | 3/2009 |
| WO | 2009069044 | A1 | 6/2009 |
| WO | 2009080197 | A1 | 7/2009 |
| WO | 2009080198 | A1 | 7/2009 |
| WO | 2009080199 | A1 | 7/2009 |
| WO | 2009080242 | A1 | 7/2009 |
| WO | 2009080248 | A1 | 7/2009 |
| WO | 2009086940 | A1 | 7/2009 |
| WO | 2009086941 | A1 | 7/2009 |
| WO | 2009086942 | A1 | 7/2009 |
| WO | 2009135599 | A1 | 11/2009 |
| WO | 2009149278 | A1 | 12/2009 |
| WO | 2009149279 | A2 | 12/2009 |
| WO | 2010009319 | A2 | 1/2010 |
| WO | 2010020363 | A1 | 2/2010 |
| WO | 2010020366 | A1 | 2/2010 |
| WO | 2010034344 | A1 | 4/2010 |
| WO | 2010078953 | A1 | 7/2010 |
| WO | 2010115548 | A1 | 10/2010 |
| WO | 2010129467 | A1 | 11/2010 |
| WO | 2011062766 | A2 | 5/2011 |
| WO | 2011069038 | A2 | 6/2011 |
| WO | 2011069094 | A1 | 6/2011 |

(56) References Cited

FOREIGN PATENT DOCUMENTS

| | | | |
|---|---|---|---|
| WO | 2011104322 | A1 | 9/2011 |
| WO | 2011107749 | A2 | 9/2011 |
| WO | 2011107750 | A2 | 9/2011 |
| WO | 2011107755 | A2 | 9/2011 |
| WO | 2011161099 | A1 | 12/2011 |
| WO | 2012000945 | A1 | 1/2012 |
| WO | 2012007539 | A1 | 1/2012 |
| WO | 2012037380 | A2 | 3/2012 |
| WO | 2012050884 | A2 | 4/2012 |
| WO | 2012118972 | A2 | 9/2012 |
| WO | 2012171575 | A1 | 12/2012 |
| WO | 2013105057 | A1 | 7/2013 |
| WO | 2013105058 | A1 | 7/2013 |
| WO | 2013105061 | A1 | 7/2013 |
| WO | 2013105063 | A1 | 7/2013 |
| WO | 2013105065 | A1 | 7/2013 |
| WO | 2013105066 | A1 | 7/2013 |
| WO | 2013138352 | A1 | 9/2013 |
| WO | 2014151200 | A2 | 9/2014 |
| WO | 2014197720 | A2 | 12/2014 |
| WO | 2015036560 | A1 | 3/2015 |
| WO | 2015036563 | A1 | 3/2015 |
| WO | 2015052065 | A1 | 4/2015 |
| WO | 2015054500 | A2 | 4/2015 |
| WO | 2015067630 | A1 | 5/2015 |
| WO | 2015067650 | A1 | 5/2015 |
| WO | 2015091415 | A1 | 6/2015 |
| WO | 2015150350 | A1 | 10/2015 |
| WO | 2015150362 | A2 | 10/2015 |
| WO | 2015150363 | A1 | 10/2015 |
| WO | 2015150364 | A1 | 10/2015 |
| WO | 2015150366 | A1 | 10/2015 |
| WO | 2015162456 | A1 | 10/2015 |
| WO | 2015162459 | A1 | 10/2015 |
| WO | 2015189117 | A1 | 12/2015 |
| WO | 2003032978 | A1 | 3/2016 |
| WO | 2016037954 | A1 | 3/2016 |
| WO | 2016066256 | A1 | 5/2016 |
| WO | 2016113205 | A1 | 7/2016 |
| WO | 2016146602 | A1 | 9/2016 |
| WO | 2016150901 | A1 | 9/2016 |
| WO | 2016188711 | A1 | 12/2016 |
| WO | 2016198342 | A1 | 12/2016 |
| WO | 2017007955 | A1 | 1/2017 |
| WO | 2017025588 | A1 | 2/2017 |
| WO | 2017027673 | A1 | 2/2017 |
| WO | 2017040864 | A1 | 3/2017 |
| WO | 2017083470 | A1 | 5/2017 |
| WO | 2017097671 | A1 | 6/2017 |
| WO | 2017097792 | A1 | 6/2017 |
| WO | 2017136757 | A1 | 8/2017 |
| WO | 2017153231 | A1 | 9/2017 |
| WO | 2017153234 | A1 | 9/2017 |
| WO | 2017153235 | A1 | 9/2017 |
| WO | 2017191105 | A1 | 11/2017 |
| WO | 2017191107 | A1 | 11/2017 |
| WO | 2017191112 | A1 | 11/2017 |
| WO | 2017191114 | A1 | 11/2017 |
| WO | 2017191115 | A1 | 11/2017 |
| WO | 2017194459 | A1 | 11/2017 |
| WO | 2018011017 | A1 | 1/2018 |
| WO | 2018015196 | A1 | 1/2018 |
| WO | 2018041771 | A1 | 3/2018 |
| WO | 2018050510 | A1 | 3/2018 |
| WO | 2018054846 | A1 | 3/2018 |
| WO | 2018073144 | A1 | 4/2018 |

OTHER PUBLICATIONS

Akerman A, et al. Computational postprocessing quantification of small bowel motility using magnetic resonance mages in clinical practice: An initial experience. J Magn Reson Imaging JMRI. Aug. 2016;44(2):277-287.

Aldasoro M, et al. Effects of Ranolazine on Astrocytes and Neurons in Primary Culture. PloS One. 2016;11(3):e0150619.

Al-Shboul OA. The importance of interstitial cells of cajal in the gastrointestinal tract. Saudi J Gastroenterol Off J Saudi Gastroenterol Assoc. Feb. 2013; 19(1):3-15.

Amir R, et al. The role of sodium channels in chronic inflammatory and neuropathic pain. J Pain Off J Am Pain Soc. May 2006;7(5 Suppl 3):S1-29.

Anthony A, et al. Early histological features of small intestinal injury induced by indomethacin. Aliment Pharmacol Ther. Feb. 1, 1993;7(1):29-40.

Bassotti G. Gastrointestinal motility disorders in inflammatory bowel diseases. World J Gastroenterol. 2014;20(1):37-44.

Best WR, et al. Development of a Crohn's disease activity index. National Cooperative Crohn's Disease Study. Gastroenterology. Mar. 1976;70(3):439-444.

Beyder A, et al. Ion channelopathies in functional GI disorders. Am J Physiol—Gastrointest Liver Physiol. Oct. 1, 2016;311(4):G581-G586.

Beyder A, et al. Loss-of-Function of the Voltage-Gated Sodium Channel NaV1.5 (Channelopathies) in Patients With Irritable Bowel Syndrome. Gastroenterology. Jun. 2014; 146(7):1659-1668.

Bickelhaupt S, et al. Correlation between morphological expansion and impairment of intra- and prelesionary motility in inflammatory small bowel lesions in patients with Crohn's disease—preliminary data. Eur J Radiol. Jul. 2014;83(7):1044-1050.

BioGPS. SCN5A (sodium voltage-gated channel alpha subunit 5) | Gene Report | BioGPS [Internet]. Accessed Mar. 1, 2023. Available from: http://biogps.org/#goto=genereport&id=6331 (1 page).

Black JA, et al. Sodium channel activity modulates multiple functions in microglia. Glia. Aug. 1, 2009;57(10):1072-1081.

Bonfiglio F, et al. A GWAS meta-analysis from 5 population-based cohorts implicates ion channel genes in the pathogenesis of irritable bowel syndrome. Neurogastroenterol Motil Off J Eur Gastrointest Motil Soc. Apr. 19, 2018;e13358.

Boyapati R, et al. Pathogenesis of Crohn's disease. F1000Prime Rep [Internet]. Apr. 2, 2015 [cited Mar. 8, 2018];7 (18 pages).

Chadda KR, et al. Sodium channel biophysics, late sodium current and genetic arrhythmic syndromes. Pflugers Arch. 2017;469(5):629-641.

Chang J, et al. Impaired Intestinal Permeability Contributes to Ongoing Bowel Symptoms in Patients With Inflammatory Bowel Disease and Mucosal Healing. Gastroenterology. Sep. 1, 2017;153(3):723-731.e1.

Chang M, et al. Intestinal and Extraintestinal Cancers Associated With Inflammatory Bowel Disease. Clin Colorectal Cancer. Mar. 2018,17(1):e29-e37.

Chiodini RJ, et al. The predominant site of bacterial translocation across the intestinal mucosal barrier occurs at the advancing disease margin in Crohn's disease. Microbiology. 2016;162(9):1608-1619.

Choi D, et al. Bowel wall thickening in patients with Crohn's disease: CT patterns and correlation with inflammatory activity. Clin Radiol. Jan. 2003;58(1):68-74.

Church PC, et al. Magnetic resonance enterography has good inter-rater agreement and diagnostic accuracy for detecting inflammation in pediatric Crohn disease. Pediatr Radiol. May 2017;47(5):565-575.

Cibor D. Endothelial dysfunction in inflammatory bowel diseases: Pathogenesis, assessment and implications. World J Gastroenterol. 2016;22(3):1067.

Cirillo, C. et al. "Enteric nervous system abnormalities in ulcerative colitis." Ulcerative Colitis—Epidemiology, Pathogenesis and Complications. IntechOpen, 2011 (pp. 29-50).

Clinicaltrials.gov. Search of: ranolazine—List Results [Internet]. Version dated Mar. 1, 2023. Available from: https://web.archive.org/web/20230301195227/https://clinicaltrials.gov/ct2/results?cond=&term=ranolazine&cntry=&state=&city=&dist= (19 pages).

Code of Federal Regulations Title 21, vol. 5, 21CFR312.32, revised Apr. 1, 2006. Available online at https://web.archive.org/web/20061206175736/http://www.accessdata.fda.gov:80/scripts/cdrh/cfdocs/cfcfr/CFRSearch.cfm?fr=312.32. (3 pages).

(56) References Cited

OTHER PUBLICATIONS

Crohn's and Colitis Foundation of America. The Facts About Inflammatory Bowel Disease [Internet]. Nov. 2014. Available from: http://www.crohnscolitisfoundation.org/assets/pdfs/updatedibdfactbook.pdf (24 pages).
Cromer WE, et al. Role of the endothelium in inflammatory bowel diseases. World J Gastroenterol. Feb. 7, 2011;17(5):578-593.
Crotti L, et al. Long QT Syndrome-Associated Mutations in Intrauterine Fetal Death. JAMA. Apr. 10, 2013;309(14):1473-1482.
Danciu I, et al. Secondary use of clinical data: the Vanderbilt approach. J Biomed Inform. Dec. 2014;52:28-35.
De Vecchis R, et al. Antiarrhythmic effects of ranolazine used both alone for prevention of atrial fibrillation and as an add-on to intravenous amiodarone for its pharmacological cardioversion: a meta-analysis. Minerva Cardioangiologica Jun. 2018; 66(3): 349-359.
Der-Silaphet T, et al. Interstitial cells of Cajal direct normal propulsive contractile activity in the mouse small intestine. Gastroenterology. Apr. 1998;114(4):724-736.
Deshmukh SH, et al. Ranolazine improves endothelial function in patients with stable coronary artery disease: Coron Artery Dis. Aug. 2009;20(5):343-347.
Detta N, et al. The multi-faceted aspects of the complex cardiac Nav1.5 protein in membrane function and pathophysiology. Biochim Biophys Acta BBA—Proteins Proteomics. Oct. 1, 2015;1854(10, Part A):1502-1509.
Dore M, et al. Pitfalls in Diagnosis of Early-Onset Inflammatory Bowel Disease. Eur J Pediatr Surg. Feb. 2018;28(01):039-043.
El Amrani F, et al. Anti-inflammatory and antioxidant effects of ranolazine on primary cultured astrocytes. Crit Care. 2014; 18(Suppl 1):p. 447.
Farrugia, G. "Ion channels as targets for treatment of gastrointestinal motility disorders." European Review for Medical and Pharmacological Sciences 12.1 (2008): 135.
FDA. Multiple Endpoints in Clinical Trials Guidance for Industry [Internet]. Jan. 2017 . Available from: https://web.archive.org/web/20190917221350/https://www.fda.gov/media/102657/download (54 pages).
FDA. Package Insert: RANEXA (ranolazine) extended-release tablets [Internet]. FDA Access Data. 2016. Available from: https://www.accessdata.fda.gov/drugsatfda_docs/label/2016/021526s029lbl.pdf (23 pages).
Fredj S, et al. Molecular basis of ranolazine block of LQT-3 mutant sodium channels: evidence for site of action. Br J Pharmacol. May 2006;148(1):16-24.
Gajendran M, et al. A comprehensive review and update on Crohn's disease. Dis Mon. Feb. 2018;64(2):20-57.
Garrick T, et al. Gastric motility is a major factor in cold restraint-induced lesion formation in rats. Am J Physiol-Gastrointest Liver Physiol. Feb. 1986;250(2):G191-G199.
GeneCards. SCN5A Gene—GeneCards | SCN5A Protein | SCN5A Antibody [Internet]. Accessed on Oct. 17, 2017. Available from: https://web.archive.org/web/20171007073757/http://www.genecards.org/cgi-bin/carddisp.pl?gene=SCN5A (19 pages).
Genetics Home Reference. SCN5A gene [Internet]. Genetics Home Reference. Accessed Jun. 27, 2017. https://web.archive.org/web/20170627205526/https://ghr.nlm.nih.gov/gene/SCN5A (5 pages).
Gong M, et al. Role of ranolazine in the prevention and treatment of atrial fibrillation: A meta-analysis of randomized clinical trials. Heart Rhythm. Jan. 2017;14(1):3-11.
Gothe F, et al. Bile acid malabsorption assessed by 7 alpha-hydroxy-4-cholesten-3-one in pediatric inflammatory bowel disease: Correlation to clinical and laboratory findings. J Crohns Colitis. Sep. 1, 2014;8(9):1072-1078.
Guerra F, et al. Ranolazine for rhythm control in atrial fibrillation: A systematic review and meta-analysis. Int J Cardiol. Jan. 2017;227:284-291.
Haase AM, et al. Regional gastrointestinal transit times in severe ulcerative colitis. Neurogastroenterol Motil. Feb. 2016;28(2):217-224.
Hahnemann ML, et al. Quantitative assessment of small bowel motility in patients with Crohn's disease using dynamic MRI. Neurogastroenterol Motil. Jun. 1, 2015;27(6):841-848.
Harris, P. A., et al. "Research electronic data capture (REDCap)—a metadata-driven methodology and workflow process for providing translational research informatics support." Journal of biomedical informatics 42.2 (2009):377-381.
Harvey, R. F., et al. "A simple index of Crohn's-disease activity." The Lancet 315.8167 (1980): 514.
Rumessen JJ, et al. Ulcerative colitis: ultrastructure of interstitial cells in myenteric plexus. Ultrastruct Pathol. Oct. 2010;34(5):279-287.
Saito YA, et al. Sodium channel mutation in irritable bowel syndrome: evidence for an ion channelopathy. Am J Physiol Gastrointest Liver Physiol. Feb. 2009;296(2):G211-218.
Sanovic S, et al. Damage to the Enteric Nervous System in Experimental Colitis. Am J Pathol. Oct. 1999; 155(4):1051-1057.
Satoh H, et al. Role of bacteria in gastric ulceration produced by indomethacin in the rat: Cytoprotective action of antibiotics. Gastroenterology. Mar. 1, 1983;84(3):483-489.
Schram G, et al. Ranolazine: Ion-channel-blocking actions and in vivo electrophysiological effects. Br J Pharmacol. Aug. 2004;142(8):1300-1308.
Schwartz DA, et al. The natural history of fistulizing Crohn's disease in Olmsted County, Minnesota. Gastroenterology. Apr. 2002;122(4):875-880.
Shinlapawittayatom K, et al. A common SCN5A polymorphism modulates the biophysical defects of SCN5A mutations. Heart Rhythm. Mar. 2011;8(3):455-462.
Singer AAM, et al. Fistulizing Crohn's Disease Presenting After Surgery on a Perianal Lesion. Pediatrics. Mar. 1, 2016;137(3):e20152878.
Sohn B, et al. Intestinal lesions in pediatric Crohn disease: comparative detectability among pulse sequences at MR enterography. Pediatr Radiol. Jul. 2014;44(7):821-830.
Spiegel BMR, et al. Development of the NIH Patient-Reported Outcomes Measurement Information System (PROMIS) gastrointestinal symptom scales. Am J Gastroenterol. Nov. 2014;109(11):1804-1814.
Stratton Do, J. et al. Ulcerative Colitis Pathology: Overview, Epidemiology, Etiology. Apr. 13, 2017. Available from: https://emedicine.medscape.com/article/2005396-overview (15 pages).
Suekane T, et al. Phenotypic change and accumulation of smooth muscle cells in strictures in Crohn's disease: relevance to local angiotensin II system. J Gastroenterol. Aug. 1, 2010;45(8):821-830.
Sullivan S, et al. Downregulation of sodium transporters and NHERF proteins in IBD patients and mouse colitis models: potential contributors to IBD-associated diarrhea. Inflamm Bowel Dis. Feb. 2009;15(2):261-274.
Surawicz CM. Mechanisms of diarrhea. Curr Gastroenterol Rep. Aug. 2010; 12(4):236-241.
Takeuchi K, et al. Increased microvascular permeability and lesion formation during gastric hypermotility caused by indomethacin and 2-deoxy-D-glucose in the rat. J Clin Gastroenterol. 1990;12 Suppl 1:S76-84.
Takeuchi K, et al. Pathogenic Importance of Intestinal Hypermotility in NSAID-Induced Small Intestinal Damage in Rats. Digestion. 2002;66(1):30-41.
Takeuchi K, et al. Possible mechanisms involved in gastric hypermotility caused by indomethacin in the rat: Role of glycoprivic response. Dig Dis Sci. Aug. 1990;35(8):984-992.
Teng S, et al. Vagal Stimulation Facilitates Improving Effects of Ranolazine on Cardiac Function in Rats with Chronic Ischemic Heart Failure. Curr Mol Med. 2018;18(1):36-43.
Terruzzi I, et al. Ranolazine promotes muscle differentiation and reduces oxidative stress in C2C12 skeletal muscle cells. Endocrine. 2017;58(1):33-45.
Trivedi C, et al. Efficacy of ranolazine in preventing atrial fibrillation following cardiac surgery: Results from a meta-analysis. J Arrhythmia. Jun. 2017;33(3):161-166.
Verstraelen TE, et al. The role of the SCN5A-encoded channelopathy in irritable bowel syndrome and other gastrointestinal disorders. Neurogastroenterol Motil. Jul. 2015;27(7):906-913.

(56) References Cited

OTHER PUBLICATIONS

Villanacci V, et al. Enteric nervous system abnormalities in inflammatory bowel diseases. Neurogastroenterol Motil Off J Eur Gastrointest Motil Soc. Sep. 2008;20(9):1009-1016.
Weissenborn U, et al. Indometacin-Induced Gastrointestinal Lesions in Relation to Tissue Concentration, Food Intake and Bacterial Invasion in the Rat. Pharmacology. 1985;30(1):32-39.
Wu P, et al. Risk of cardiovascular disease in inflammatory bowel disease. Exp Ther Med. Feb. 2017; 13(2):395-400.
Yamaci RF, et al. Neonatal Nav1.5 protein expression in normal adult human tissues and breast cancer. Pathol—Res Pract. Aug. 2017;213(8):900-907.
Zeng X, et al. Efficacy and Safety of Ranolazine in Diabetic Patients: A Systematic Review and Meta-analysis. Ann Pharmacother. 2017, 415-424.
Hatoum OA, et al. Acquired microvascular dysfunction in inflammatory bowel disease: Loss of nitric oxide-mediated vasodilation. Gastroenterology. Jul. 2003;125(1):58-69.
Heagerty, P.J. et al. "Time-dependent ROC curves for censored survival data and a diagnostic marker." Biometrics 56.2 (2000): 337-344.
Henström, M. et al. "Genetics of irritable bowel syndrome." Molecular and cellular pediatrics 3.1 (2016): 1-5.
House CD, et al. Voltage-gated Na+ channel SCN5A is a key regulator of a gene transcriptional network that controls colon cancer invasion. Cancer Res. Sep. 1, 2010;70(17):6957-6967.
Huang W, et al. Structure-based assessment of disease-related mutations in human voltage-gated sodium channels. Protein Cell. Jun. 2017;8(6):401-438.
Hulzinga JD, et al. W/kit gene required for interstitial cells of Cajal and for intestinal pacemaker activity. Nature. Jan. 1995;373(6512):347-349.
Inaba Y, et al. Prediction of future cardiovascular outcomes by flow-mediated vasodilatation of brachial artery: a meta-analysis. Int J Cardiovasc Imaging. Aug. 2010;26(6):631-640.
International Preliminary Report on Patentability for Application No. PCT/US2021/037086 dated Dec. 13, 2022 (5 pages).
International Search Report and Written Opinion for Application No. PCT/US2021/037086 dated Oct. 6, 2021 (13 pages).
Irvine, E. J., et al. "The Short Inflammatory Bowel Disease Questionnaire: A Quality of Life Instrument for Community Physicians Managing Inflammatory Bowel Disease." American Journal of Gastroenterology (Springer Nature) 91.8 (1996) 1571-1578.
Jones A, et al. Human macrophage SCN5A activates an innate immune signaling pathway for antiviral host defense. J Biol Chem. Dec. 19, 2014;289(51):35326-35340.
Kegg TO1001: SCN5A [Internet]. Accessed on Mar. 1, 2023. Available from: https://web.archive.org/web/20230301204733/https://www.genome.jp/dbget-bin/www_bget?hsa+SCN5A (4 pages).
Kochar B, et al. Evaluation of Gastrointestinal Patient Reported Outcomes Measurement Information System (Gi-PROMIS) Symptom Scales in Subjects With Inflammatory Bowel Diseases. Am J Gastroenterol. Jan. 2018;113(1):72-79.
Komperød MJ, et al. Persistent symptoms in patients with Crohn's disease in remission: An exploratory study on the role of diet. Scand J Gastroenterol. Nov. 23, 2017, 573-578.
Konaka A, et al. Roles of Enterobacteria, Nitric Oxide and Neutrophil in Pathogenesis of Indomethacin-Induced Small Intestinal Lesions in Rats. Pharmacol Res. Dec. 1, 1999;40(6):517-524.
Koo MWL, et al. Effects of cold-restraint stress on gastric ulceration and motility in rats. Pharmacol Biochem Behav. Oct. 1, 1986;25(4):775-779.
Kristinsson, J. O., et al. "Gastroparesis in patients with inactive Crohn's disease: a case series." BMC Gastroenterology 7 (2007): 11.
Kroenke, K. et al. "The PHQ-9: validity of a brief depression severity measure." Journal of general internal medicine 16.9 (2001): 606-613.
Kumar P, et al. Predicting the effects of coding non-synonymous variants on protein function using the SIFT algorithm. Nat Protoc. 2009;4(7):1073-1081.
Lakhan SE, et al. Neuroinflammation in inflammatory bowel disease. J Neuroinflammation. Jul. 8, 2010;7:37.
Lang J, et al. Diaphragm disease: pathology of disease of the small intestine induced by non-steroidal anti-inflammatory drugs. J Clin Pathol. May 1988;41(5):516-526.
Laube R, et al. Oral and upper gastrointestinal Crohn's disease: Upper GI Crohn's Disease. J Gastroenterol Hepatol. Feb. 2018;33(2):355-364.
Lek M, et al. Analysis of protein-coding genetic variation in 60,706 humans. Nature. 2016 18;536(7616):285-291.
Lichtenstein GR, et al. ACG Clinical Guideline: Management of Crohn's Disease in Adults. Am J Gastroenterol. Apr. 2018;113(4):481-517.
Locke GR, et al. Gastrointestinal Symptoms in Families of Patients with an SCN5A-Encoded Cardiac Channelopathy: Evidence of an Intestinal Channelopathy. Am J Gastroenterol. Jun. 2006;101(6):1299-1304.
Makielski JC. Late sodium current: A mechanism for angina, heart failure, and arrhythmia. Trends Cardiovasc Med. Feb. 2016;26(2):115-122.
Malykhina AP, et al. Inflammation-induced "channelopathies" in the gastrointestinal smooth muscle. Cell Biochem Biophys. 2004;41(2):319-330.
Manetti M, et al. Telocytes are reduced during fibrotic remodelling of the colonic wall in ulcerative colitis. J Cell Mol Med. Jan. 2015;19(1):62-73.
Menys A, et al. Quantified terminal ileal motility during MR enterography as a potential biomarker of Crohn's disease activity: a preliminary study. Eur Radiol. Nov. 2012;22(11):2494-2501.
Menys A, et al. Small bowel strictures in Crohn's disease: a quantitative investigation of intestinal motility using MR enterography. Neurogastroenterol Motil Off J Eur Gastrointest Motil Soc. Dec. 2013;25(12):967-e775.
Mourad FH, et al. Impairment of Small Intestinal Function in Ulcerative Colitis: Role of Enteric Innervation. J Crohns Colitis. Mar. 1, 2017;11(3):369-377.
Neshatian, L., et al. "Ranolazine inhibits voltage-gated mechanosensitive sodium channels in human colon circular smooth muscle cells." American Journal of Physiology-Gastrointestinal and Liver Physiology 309.6 (2015): G506-G512.
Neunlist M, et al. Changes in chemical coding of myenteric neurones in ulcerative colitis. Gut. Jan. 2003;52(1):84-90.
Odille F, et al. Quantitative assessment of small bowel motility by nonrigid registration of dynamic MR images. Magn Reson Med. Sep. 2012;68(3):783-793.
Olivotto I, et al. Efficacy of Ranolazine in Patients With Symptomatic Hypertrophic Cardiomyopathy: The RESTYLE-HCM Randomized, Double-Blind, Placebo-Controlled Study. Circ Heart Fail. Jan. 2018;11(1):e004124.
Osorio N, et al. Specialized Functions of Nav1.5 and Nav1.9 Channels in Electrogenesis of Myenteric Neurons in Intact Mouse Ganglia. J Neurosci. Apr. 9, 2014;34(15):5233-5244.
Peng J, et al. Expression of voltage-gated sodium channel Nav1.5 in non-metastatic colon cancer and its associations with estrogen receptor (ER)-β expression and clinical outcomes. Chin J Cancer [Internet]. Dec. 2017;36(1).
Plumb AA, et al. Magnetic resonance imaging-quantified small bowel motility is a sensitive marker of response to medical therapy in Crohn's disease. Aliment Pharmacol Ther. Aug. 2015;42(3):343-355.
Porcher C, et al. Deficiency of interstitial cells of Cajal in the small intestine of patients with Crohn's disease. Am J Gastroenterol. Jan. 2002;97(1):118-125.
Principi M, et al. Endothelial function and cardiovascular risk in active inflammatory bowel diseases. J Crohns Colitis. Nov. 2013;7(10):e427-e433.
PubChem-CID-56959, Create Date: Aug. 8, 2008 (Aug. 8, 2008), 3 pages.

(56) References Cited

OTHER PUBLICATIONS

Pulley JM, et al. Accelerating Precision Drug Development and Drug Repurposing by Leveraging Human Genetics. Assay Drug Dev Technol. Apr. 2017; 15(3):113-119.
Quigley EMM. Overlapping irritable bowel syndrome and inflammatory bowel disease: less to this than meets the eye? Ther Adv Gastroenterol. Mar. 2016;9(2):199-212.
Rana SV, et al. Relationship of cytokines, oxidative stress and GI motility with bacterial overgrowth in ulcerative colitis patients. J Crohns Colitis. Aug. 2014;8(8):859-865.
Ranexa® (ranolazine) | Official Patient Site [Internet]. Accessed Dec. 17, 2017. Available online at https://web.archive.org/web/20171217203543/http://www.ranexa.com/ (8 pages).
Rani, R.A. et al. Irritable bowel syndrome and inflammatory bowel disease overlap syndrome: pieces of the puzzle are falling into place. Intest Res. Oct. 2016;14(4):297-304.
Reddy BM, et al. Ranolazine: a new approach to treating an old problem. Tex Heart Inst J. 2010;37(6):641-647.
Rieder F, et al. Intestinal fibrosis in inflammatory bowel disease—Current knowledge and future perspectives. J Crohns Colitis. Dec. 2008;2(4):279-290.
Robert A, et al. Resistance of germfree rats to indomethacin-induced intestinal lesions. Prostaglandins. Aug. 1977;14(2):333-341.
Rumessen JJ, et al. Crohn's disease of the colon: ultrastructural changes in submuscular interstitial cells of Cajal. Cell Tissue Res. Feb. 1, 2011;343(2):421-428.

METHODS OF TREATMENT FOR GASTROINTESTINAL MOTILITY DISORDERS

CROSS-REFERENCE TO RELATED APPLICATIONS

This patent application is the U.S. national stage entry, under 35 U.S.C. § 371, of International Application Number PCT/US2021/037086, filed Jun. 11, 2021, which claims priority to U.S. Provisional Application No. 63/038,326, filed Jun. 12, 2020, the entire contents of each of which are hereby incorporated by reference.

STATEMENT REGARDING FEDERALLY SPONSORED RESEARCH

This invention was made with government support under grant 5UL1TR002243-03 awarded by the National Center for Advancing Translational Sciences. The government has certain rights in the invention.

FIELD

This disclosure relates to methods of treatment for gastrointestinal motility disorders.

INTRODUCTION

Crohn's Disease (CD) is an idiopathic inflammatory disorder of unknown etiology with genetic, immunologic, and environmental influences. CD can affect any part of the gastrointestinal (GI) tract, affecting some areas of the GI tract and leaving others untouched. CD patients experience a lifelong cycle of a relapsing-and-remitting disease course requiring frequent corticosteroids, and/or escalation in immunosuppressive treatment; approximately half of patients will require surgery within 10 years of diagnosis. Even patients who achieve remission can experience persistent, refractory diarrhea or other symptoms such as abdominal pain, significantly affecting their quality of life and ability to work. Over 780,000 Americans are affected by CD and the worldwide incidence has been steadily increasing.

The current standard of care for patients with CD is individualized and based on disease location, disease severity, disease-associated complications, and future disease prognosis. Therapeutic approaches are a sequential continuum to treat "acute disease" or "induce clinical remission," and then to "maintain response/remission," the overall treatment goal being to control inflammation and symptoms arising from active inflammation. Medical therapies used to treat CD includes the categories of 5-aminosalicylates (5-ASA), antibiotics, corticosteroids, immunomodulators, and biologics (the anti-TNF agents infliximab, adalimumab, certolizumab pegol; agents targeting leukocyte trafficking, including vedolizumab, natalizumab; and the anti-p40 (anti-IL-12/23) antibody, ustekinumab). Diarrhea and/or abdominal pain that is not responsive to standard therapies may be treated with lomotil or other opioids which have significant side effects and risk. In addition to opioids, the immunosuppressive therapies also have substantial negative side effects. Despite significant medical advancements in the treatment of CD, there remains a considerable unmet medical need for safe, effective, oral treatments for CD. Further, there remains a need for a novel method of treatment for gastrointestinal motility disorders such as CD that target other systems in addition to the immune system, such as the gastrointestinal system itself.

SUMMARY

In an aspect, the disclosure relates to a method for treating a gastrointestinal motility disorder or reducing symptoms thereof in a subject in need thereof. The method may include administering to the subject a therapeutically effective amount of a compound of Formula I:

(I)

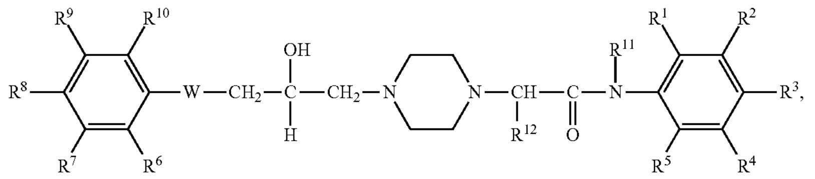

or a pharmaceutically acceptable ester or salt thereof, wherein: R1, R2, R3, R4 and R5 are each independently hydrogen, lower alkyl, lower alkoxy, cyano, trifluoromethyl, halo, lower alkylthio, lower alkyl sulfinyl, lower alkyl sulfonyl, or N-optionally substituted alkylamido (except that when R1 is methyl, R4 is not methyl); or R2 and R3 taken together form —OCHO2O—; R6, R7, R8, R9 and R10 are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, di (lower alkyl) amino; or R6 and R7 together form —CH═CH—CH═CH—; or R7 and R8 together form —OCH2O—; R11 and R12 are each independently hydrogen or lower alkyl; and Wis oxygen or sulfur; and, wherein the compound decreases contractility of gastrointestinal tract muscles. In some embodiments, the compound may be administered in the form of a composition wherein the composition comprises a pharmaceutically acceptable carrier. In some embodiments, the compound may be a compound of Formula II:

(II)

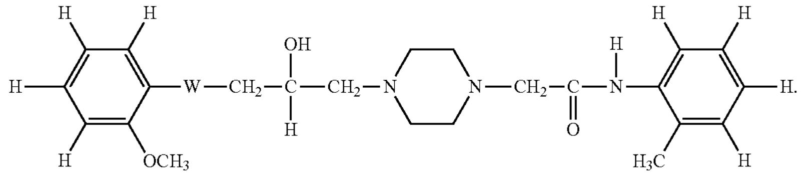

In some embodiments, the method comprises administering the pharmaceutically acceptable salt of the compound. In some embodiments, the gastrointestinal motility disorder may be associated with Crohn's Disease. In some embodiments, the compound may be administered orally. In some embodiments, the composition may comprise about 500 mg to about 1000 mg of the compound. In some embodiments, a daily dosage may be about 2000 mg of the compound. In some embodiments, a daily dosage may be about 1000 mg of the compound. In some embodiments, the composition may comprise about 1000 mg of the compound. In some embodiments, the composition may comprise about 500 mg of the compound. In some embodiments, the compound may be administered to the subject more than once per day. In some embodiments, the compound may be administered about 6 hours to about 12 hours apart. In some embodiments, the compound may be administered once in the morning and the compound is administered once in the evening. In some embodiments, following administration of the compound to the subject, abdominal pain may be reduced. In some embodiments, following administration of the compound to the subject, emotional disorders in the subject may be reduced. In some embodiments, the emotional disorders may comprise anxiety, depression, anhedonia, antisocial disorder, agoraphobia, or combinations thereof. In some embodiments, following administration of the compound to the subject, Crohn's disease symptoms in the subject may be reduced. In some embodiments, the Crohn's disease symptoms may comprise diarrhea, fever, fatigue, abdominal pain, abdominal cramping, blood in stool, mouth sores, reduced appetite, weight loss, pain near or around the anus, drainage near or around the anus, fistulas, bloating, bowel obstruction, nausea, vomiting, flatulence, or a combination thereof. In some embodiments, administration of the compound may result in inhibition of a late sodium current of an action potential in gastrointestinal system cells. In some embodiments, intracellular sodium may be reduced in gastrointestinal system cells. In some embodiments, intracellular calcium may be reduced in the gastrointestinal system cells. In some embodiments, intracellular ion homeostasis of gastrointestinal system cells may be restored. In some embodiments, the gastrointestinal system cells may comprise intestinal smooth muscle cells (SMCs), motor neurons, sensory neurons, fibroblasts, interstitial cells of Cajal (ICC), epithelial cells, goblet cells, or combinations thereof. In some embodiments, the compound may be administered without food and at least 30 minutes prior to food consumption. In some embodiments, the subject may have active Crohn's disease. In some embodiments, the subject may have Crohn's disease that is in remission and exhibits diarrhea before administration of the compound. In some embodiments, the subject may exhibit ≥3 loose stools per day on average before administration of the compound. In some embodiments, the compound may be administered concomitantly with a secondary treatment for Crohn's disease. In some embodiments, the secondary treatment for Crohn's disease may comprise anti-inflammatories, immunosuppressants, antibiotics, analgesics, iron supplements, vitamin B-12 shots, calcium supplements, vitamin D supplements, or combinations thereof. In some embodiments, the anti-inflammatories may comprise corticosteroids, 5-aminosalicylates, or combinations thereof. In some embodiments, the immunosuppressants may comprise Azathioprine, Infliximab, Methotrexate, Natalizumab, Vedolizumab, Ustekinumab, or combinations thereof. In some embodiments, the subject may have a sodium voltage-gated channel alpha subunit 5 (SCN5A) channelopathy. In some embodiments, the channelopathy may increase sodium current. In some embodiments, SCN5A may be expressed in intestinal SMCs and/or ICC. In some embodiments, the subject may have uncoordinated temporal and spatial intestinal smooth muscle contractions and relaxations. In some embodiments, temporal and spatial coordination of intestinal smooth muscle contractions and relaxations may be restored following treatment. In some embodiments, the subject may not be constipated. In some embodiments, the compound is ranolazine.

The disclosure provides for other aspects and embodiments that will be apparent in light of the following detailed description and accompanying figures.

BRIEF DESCRIPTION OF THE DRAWINGS

FIG. 4A shows disruptions in Nav1.5 signaling in cells of the GI tract and FIG. 4B shows altered contractility/motility of the GI tract and clinical presentations of a gastrointestinal motility disorder.

DETAILED DESCRIPTION

Figure 1:
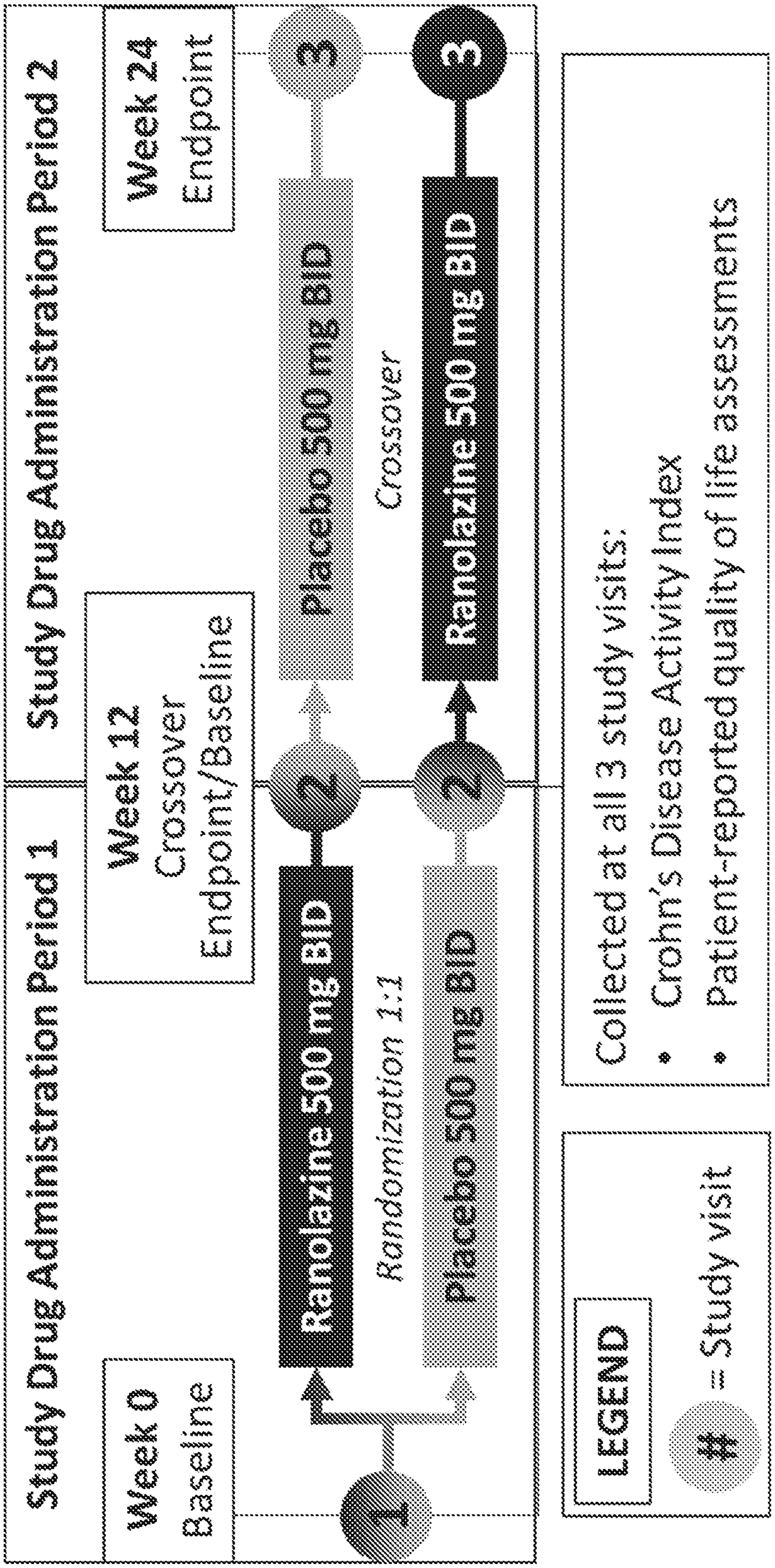
FIG. 1 is a schematic of the clinical trial.

Described herein are methods of treating and/or alleviating symptoms of a gastrointestinal (GI) motility disorder, such as that associated with/caused by Crohn's Disease (CD). Current therapies for the treatment of CD aim to control inflammation and symptoms caused by inflammation through immunosuppression. As a result of suppressing the immune system, these therapies have significant, unwanted side effects. Ranolazine, a sodium channel blocker, may improve CD symptoms by acting on one or more interrelated pathways or factors, such as inflammation, endothelial dysfunction, gut motility, and genetic or environmental factors. The methods detailed herein include administering a compound of Formula I to treat or reduce symptoms of a GI motility disorder.

The disclosed methods may restore normal, coordinated gut motility. For example, administering a compound of Formula I to a patient with a GI motility disorder may restore normal, coordinated gut motility. GI dysmotility is a feature of CD, where GI dysmotility can include hypermotility or increased contractility. GI motility is a result of a coordinated, cooperative interaction that includes interstitial cells of Cajal (ICC) and intestinal smooth muscle cells (SMCs). These cells express the sodium channel protein type 5 subunit alpha (Nav1.5), a target of ranolazine. The disclosed methods may relate to the use of a compound of Formula I for restoration of the calibration and synchronicity of the gut's motility mechanism and reducing CD-associated symptoms, such as diarrhea.

The methods herein may reduce inflammation associated with GI motility disorders. For example, administering a compound of Formula I to a patient suffering from a GI motility disorder may reduce inflammation. Transmural inflammation of the gastrointestinal tract is considered a hallmark of CD and is implicated in endothelial dysfunction and gut dysmotility. In addition, inflammation can induce channelopathies in the GI smooth muscle and it has also been suggested that changes in sodium channels in sensory neurons may play a role in inflammatory pain. Therefore, sodium channel blockers, like ranolazine, may modulate inflammatory pain.

Also described herein are methods that may reduce endothelial dysfunction associated with GI motility disorders. For instance, administering a compound of Formula I to a patient with a GI motility disorder may reduce endothelial cell dysfunction. Endothelial dysfunction may occur when there is impairment in homeostatic functions of endothelium, ranging from control of vascular tone and leukocyte trafficking to surveillance of platelet adhesion and thrombus formation. The compounds of Formula I may improve endothelial-dependent vasodilatation, a marker of endothelial dysfunction, in coronary artery disease patients. The disclosed methods may relate to the use of a compound of Formula I to potentially improve endothelial function in CD patients, which could lead to reduction of CD symptoms.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" or "approximately" as used herein as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Alternatively, "about" can mean within 3 or more than 3 standard deviations, per the practice in the art. Alternatively, such as with respect to biological systems or processes, the term "about" can mean within an order of magnitude, in some embodiments within 5-fold, and in some embodiments within 2-fold, of a value.

The terms "active ingredient" or "active pharmaceutical ingredient" as used herein refer to a pharmaceutical agent, active ingredient, compound, or substance, compositions, or mixtures thereof, that provide a pharmacological, often beneficial, effect.

The term "adverse event" as used herein refers to any unexpected, inappropriate medical occurrence in a patient or study participant or participant or clinical investigation subject administered a pharmaceutical product, and which does not necessarily have a causal relationship with the treatment. An adverse event can therefore be any unfavorable and unintended sign (including an abnormal laboratory finding), symptom, or disease temporally associated with the use of a medicinal (investigational) product, whether or not considered related to the medicinal (investigational) product.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (Biometrics 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, in some embodiments a value that corresponds to the 25th percentile, the 50th percentile or the 75th percentile, and in some embodiments the 75th percentile. Such statistical analyses may be performed using any method known in the art and can be implemented through any number of commercially available software packages (e.g., from Analyse-it Software Ltd., Leeds, UK; StataCorp LP, College Station, TX; SAS Institute Inc., Cary, NC.). The healthy or normal levels or ranges for a target or for a protein activity may be defined in accordance with standard practice. A control may be a subject or cell without an inhibitor as detailed herein. A control may be a subject, or a sample therefrom, whose disease state is known. The subject, or sample therefrom, may be healthy, diseased, diseased prior to treatment, diseased during treatment, or diseased after treatment, or a combination thereof.

The term "dose" as used herein denotes any form of the active ingredient formulation or composition that contains an amount sufficient to produce a therapeutic effect with at least a single administration. "Formulation" and "compound" are used interchangeably herein.

The term "dosage" as used herein refers to the administering of a specific amount, number, and frequency of doses over a specified period of time, typically 1 day.

The terms "gastrointestinal," "gut," and "GI" are used herein interchangeably and refer to the stomach, large intestines (or colon), small intestines, anus, and can include the esophagus.

The term "prophylaxis" refers to preventing or reducing the progression of a disorder, either to a statistically significant degree or to a degree detectable to one skilled in the art.

"Sample" or "test sample" as used herein can mean any sample in which the presence and/or level of a target is to be detected or determined or any sample comprising an inhibitor as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Subject," "study participant," "subject," "participant," and "patient" as used herein interchangeably refers to any vertebrate, including, but not limited to, a mammal that wants or is in need of the herein described compounds, compositions or methods. The subject may be a human or a non-human. The subject may be a vertebrate. The subject may be a mammal. The mammal may be a primate or a non-primate. The mammal can be a non-primate such as, for example, cow, pig, camel, llama, hedgehog, anteater, platypus, elephant, alpaca, horse, goat, rabbit, sheep, hamsters, guinea pig, cat, dog, rat, and mouse. The mammal can be a primate such as a human. The mammal can be a non-human primate such as, for example, monkey, cynomolgus monkey, rhesus monkey, chimpanzee, gorilla, orangutan, and gibbon. The subject may be of any age or stage of development, such as, for example, an adult, an adolescent, or an infant. The subject may be male. The subject may be female. In some embodiments, the subject has a specific genetic marker. The subject may be undergoing other forms of treatment.

"Treatment" or "treating" when referring to protection of a subject from a disease, means suppressing, repressing, reversing, alleviating, ameliorating, or inhibiting the progress of disease, or completely eliminating a disease. A treatment may be either performed in an acute or chronic way. The term also refers to reducing the severity of a disease or symptoms associated with such disease prior to affliction with the disease. Preventing the disease involves administering a composition or compound of the present disclosure to a subject prior to onset of the disease. Suppressing the disease involves administering a composition or compound of the present disclosure to a subject after induction of the disease but before its clinical appearance. Repressing or ameliorating the disease involves administering a composition or compound of the present disclosure to a subject after clinical appearance of the disease.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics, chemistry, and protein and nucleic acid chemistry described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. Gastrointestinal Motility Disorder

The terms "gastrointestinal motility disorder" and "GI motility disorder" as used interchangeably herein, refer to an inflammatory bowel disease (IBD) that causes inflammation of any part of the gastrointestinal (GI) tract. The GI motility disorder may be genetically inherited. The GI motility disorder may be caused by an autoimmune disease or immune system dysfunction. The GI motility disorder may be a chronic condition. The GI motility disorder may cause patches of inflammation. The GI motility disorder can cause inflammation in and affect mucosa, submucosa, muscularis externa, and/or serosa of the GI tract. The GI motility disorder may cause diarrhea, ulcers in the GI tract, lesions in the GI tract, bloody stools, rectal bleeding, anemia, urgent need to move bowels, abdominal pain and cramping, sensation of incomplete evacuation, unintended weight loss, constipation, fatigue, loss of appetite, nausea, fever, joint pain, night sweats, loss of normal menstrual cycle, or combinations thereof. The GI motility disorder may cause fistula formation in parts of the intestine, skin or another organ, strictures in the intestine, abscesses in abdomen, pelvis or around anal area, perforated bowel, toxic megacolon, malnutrition, extraintestinal complications (e.g. sores/rashes, joint swelling/pain, kidney stones, osteoporosis, liver disease), increased risk of colon cancer, deep vein thrombosis, pulmonary embolism and primary sclerosing cholangitis, or combinations thereof. The GI motility disorder may be Crohn's disease (CD). The GI motility disorder may have altered GI motility in the large intestine, colon, small intestine, stomach, gallbladder, or combinations thereof. The altered motility may be stomach dysmotility, hepatobiliary tree dysmotility, small bowel dysmotility, anorectum dysmotility, or combinations thereof. The dysmotility may cause dyspeptic symptoms, gallstones, delayed transit, abnormal sensations, incontinence, or combinations thereof. As used herein, "dysmotility," also known as "motility dysfunction," refers to the muscles of the digestive system not functioning as they should that may result in a change in the speed, strength or coordination of the muscles of the esophagus, stomach, small intestine and/or the large intestine. "Normal motility" as used herein refers to the muscles of the digestive system functioning as they should; a system of coordinated, orderly muscle contractions from the beginning to the end of the digestive system that facilitates digestion. Dysmotility can result in poor or spastic propulsion of food through the esophagus and stomach, poor or spastic propulsion of chyme through the small intestine, and poor or spastic propulsion of stool through the large intestine. Any change from normal motility can result in the digestive symptoms as detailed herein. The GI motility disorder may result in either increased motility or decreased motility. The altered motility may be caused by inflammation, strictures, changes in smooth muscle cell function, or combinations thereof. A subject with a GI motility disorder may have uncoordinated temporal and spatial intestinal smooth muscle contractions and relaxations.

GI motility results from coordinated interaction of multiple cooperating mechanisms and is modulated by the enteric nervous system. Both ICC and intestinal SMCs serve a fundamental role in normal GI motility and express the sodium channel alpha subunit Nav1.5. Human gastrointestinal Nav1.5 is structurally homologous to its cardiac equivalent and bears strong electrophysiological, mechanosensitive, and pharmacological similarities. ICC are ubiquitously present in the human GI tract and generate pacemaker activity through slow electrical waves. They are electrically coupled to SMCs via gap junctions ensuring coordinated GI motility.

As discussed below, GI motility disorders include Inflammatory Bowel Diseases such as Crohn's Disease and Ulcerative Colitis. GI motility disorders are different than Irritable Bowel Syndrome.

a. Sodium Voltage-Gated Channel Alpha Subunit 5 (SCN5A) and Nav1.5

SCN5A gene belongs to a family of genes that provide instructions for making sodium channels. These channels open and close at specific times to control the flow of positively charged sodium ions into cells. The sodium channels containing proteins produced from the SCN5A gene are abundant in cardiac muscle cells and play key roles in these cells' ability to generate and transmit electrical signals. These channels play a major role in signaling the start of each heartbeat, coordinating the contractions of the upper and lower chambers of the heart, and maintaining a normal heart rhythm.

SCN5A protein is found primarily in cardiac muscle and is responsible for the initial upstroke of the action potential in an electrocardiogram. This protein mediates the voltage-dependent sodium ion permeability of excitable membranes. Assuming opened or closed conformations in response to the voltage difference across the membrane, the protein forms a sodium-selective channel through which sodium ions may pass in accordance with their electrochemical gradient. Channel inactivation is regulated by intracellular calcium levels.

The voltage-gated sodium-selective ion channel Nav1.5, whose pore-forming a subunit is encoded by SCN5A, is important for cardiac function and is also expressed in the human GI tract.

b. Inflammatory Bowel Disease (IBD)

IBD is a disorder that involves chronic inflammation of the GI tract. IBD is a class of idiopathic diseases of the digestive tract that involve an autoimmune reaction. Two major types of IBD are recognized: Crohn's disease (CD) and ulcerative colitis (UC). CD, also referred to as regional enteritis, terminal ileitis or granulomatous ileocolitis, can involve any segment or segments of the digestive tract from the mouth to the anus; UC, also known as idiopathic proctocolitis, is typically limited to the colon. Where the term "inflammatory bowel disease" or "IBD" is used herein, particularly with reference to CD, It will be understood to include manifestations anywhere in the digestive tract, not exclusively in the bowel. CD and UC exhibit significant differences, but both diseases share a number of intestinal and extraintestinal manifestations, although some of these tend to occur more commonly in one disease or the other. Both CD and UC usually exhibit waxing and waning intensity and severity. When an IBD patient has symptoms indicating significant inflammation, the disease is considered to be in an "active stage" or "active"; such a patient is said to be having a "flare" of the IBD. When inflammation is of lesser severity or absent and the patient substantially asymptomatic, the disease is considered to be in "remission". In most cases, symptoms correspond well with the degree of inflammation present for either disease, although this is not universally true. In some patients, objective evidence for disease activity may be needed before administering medications with potential for significant adverse side effects.

Changes in endothelial structure and function, mediated by a complex network of chemokines, cytokines and inflammatory growth factors, are a distinctive feature of active disease and their magnitude is related to disease severity and/or gut dysmotility severity. In addition, it has been shown that human intestinal microvessels taken from chronically inflamed IBD mucosal tracts exhibit endothelial dysfunction with significant impairment of endothelium-dependent vasodilation. Endothelial dysfunction has been evaluated in IBD patients using brachial artery flow-mediated vasodilatation (FMD), a well-established measure of endothelial function; significantly lower FMD in IBD patients compared to controls has been found, suggesting endothelial dysfunction as one etiological factor of IBD. The IBD may be Crohn's disease or ulcerative colitis. The IBD is not irritable bowel syndrome (IBS). The IBD may include a sodium voltage-gated channel alpha subunit 5 (SCN5A) channelopathy. Patients with SCN5A channelopathies and known cardiac arrhythmias have an increased prevalence of functional GI disease. SCN5A channelopathies may increase sodium current and may be expressed in intestinal SMCs and ICC.

i) Crohn's Disease (CD)

CD is an idiopathic inflammatory disorder of unknown etiology with genetic, immunologic, and environmental influences. CD can affect any part of the GI tract, affecting some areas of the GI tract and leaving others untouched. The pathology of CD is characterized by transmural infiltration of lymphocytes and macrophages, granulomas, fissuring ulceration, and submucosal fibrosis. The transmural inflammatory process of CD predisposes patients to the formation of fistulas and it has been estimated that approximately 35% of patients will have at least 1 fistula during the course of their disease. GI dysmotility is a feature of CD and is interrelated with the other features of the disease. For example, multiple studies have shown inflammatory effects to be correlated with reduced intestinal motility; studies using MR enterography have found a significant difference in terminal ileum motility in patients with small bowel CD compared with healthy subjects, and when comparing inflamed and non-inflamed small bowel segments of CD patients. Hypermotility and gastrointestinal lesions also have a close relationship. The collective results of several rat studies indicate that intestinal hypermotility with its high-amplitude contractions likely disrupts the mucus layer of the intestines, interrupting the host defense barrier, exposing the luminal contents to the epithelium and allowing bacterial invasion of the mucosa, which then triggers an inflammatory response. "Hypermotility" as used herein refers to abnormal or excessive movement, such as excessive motility of all or part of the GI tract. Instances of severe gastrointestinal dysmotility have been reported in CD patients without clinically active disease (no active inflammation or mechanical obstruction) as well. Standard treatments for CD may include aminosalicylates, corticosteroids, immunomodulators, antibiotics, biologic therapies, and antidiarrheals.

In some embodiments, physiological features of CD may include inflammation affecting any part of GI tract from mouth to anus, healthy parts of intestine mixed in between inflamed areas of inflammation known as "patches," inflammation may extend through the entire thickness of the bowel wall, gut dysmotility, stomach dysmotility, dyspeptic symptoms, hepatobiliary tree dysmotility, gallstones, small bowel dysmotility, delayed transit, anorectum dysmotility, abnormal sensations, and incontinence. In some embodiments, the CD may affect the ileum (end of small intestine). In some embodiments, symptoms of CD can include diarrhea, abdominal pain, rectal bleeding, urgent need to move bowels, sensation of incomplete evacuation, fever, loss of appetite, weight loss, fatigue, night sweats, and loss of normal menstrual cycle. In some embodiments, complications of CD may include fistula to another part of intestine, skin or another organ, stricture in intestine, abscess in abdomen, pelvis or around anal area, perforated bowel, toxic megacolon, malnutrition, extraintestinal complications (e.g. sores/rashes, joint swelling/pain, kidney stones, osteoporosis, liver disease), increased risk of colon cancer, deep vein thrombosis, pulmonary embolism, and primary sclerosing cholangitis. In some embodiments, the CD can be caused by interactions between genetic predisposition, immune system disturbance and environmental triggers, brain/gut disturbance, dysfunctional microbiome, and/or environmental triggers (e.g., smoking, viruses, stress, antibiotics, NSAIDs, appendicitis, certain foods). In some embodiments, CD can be diagnosed by blood and stool tests for inflammatory biomarkers, upper endoscopy, colonoscopy, and/or imaging (e.g. CT or MRI).

In some embodiments, Formula I or Formula II compounds or compositions as detailed herein, or at least one component thereof, may reduce the CD symptoms. In some embodiments, Formula I or Formula II compounds or compositions as detailed herein, or at least one component thereof, may reduce diarrhea, fever, fatigue, abdominal pain, abdominal cramping, blood in stool, mouth sores, reduced appetite, weight loss, pain near or around the anus, drainage near or around the anus, fistulas, bloating, bowel obstruction, nausea, vomiting, flatulence, or a combination thereof.

In some embodiments, the subject may have active CD. In some embodiments, the subject may have CD that is in remission and exhibits diarrhea before administration of the composition or compound. In some embodiments, the subject may have CD that is in remission.

ii) Ulcerative Colitis (UC)

UC is a chronic disease of the large intestine that results in inflammation of the lining of the colon and development of tiny open sores, or ulcers in the colon. The stomach is not involved in UC. UC is caused by an overactive immune system. Standard treatments for CD may include aminosalicylates, corticosteroids, immunomodulators, antibiotics, biologic therapies, and antidiarrheals. In some embodiments, physiological features of UC may include inflammation only affecting the colon, continuous inflammation rather than patches, begins in the rectum and lower colon that can spread continuously to involve entire colon, inflammation only affecting the innermost lining of the colon, gut dysmotility, small bowel dysmotility associated with delayed transit, colon dysmotility that is associated with diarrhea in both the active phase and during remission, anorectum dysmotility that is related to tenesmus. In some embodiments, symptoms of UC can include diarrhea, abdominal pain, rectal bleeding, urgent need to move bowels, sensation of incomplete evacuation, fever, loss of appetite, weight loss, fatigue, night sweats, and loss of normal menstrual cycle. In some embodiments, complications of UC may include perforated bowel, toxic megacolon, severe dehydration, extraintestinal complications (e.g., sores/rashes, joint swelling/pain, kidney stones, osteoporosis, liver disease), increased risk of colon cancer, deep vein thrombosis, pulmonary embolism, and primary sclerosing cholangitis. In some embodiments, UC can be caused by interactions between genetic predisposition, immune system disturbance and environmental triggers, brain/gut disturbance, dysfunctional microbiome, and/or environmental triggers (e.g., smoking, viruses, stress, antibiotics, NSAIDs, appendicitis, certain foods). In some embodiments, UC can be diagnosed by blood and stool tests for inflammatory biomarkers, sigmoidoscopy, colonoscopy, and/or imaging (e.g., CT or MRI).

3. Irritable Bowel Syndrome (IBS)

IBS is a functional gastrointestinal disorder, classified as a syndrome (group of symptoms) rather than a disease. IBS is not related to a GI motility disorder, IBD, CD, or UC. IBS does not cause inflammation in the digestive tract. IBS can be caused by brain/gut disturbances, genetics, microbiome changes, environmental triggers: foods, stress, hormonal changes, and/or medications. There is no sign of disease or abnormality during examination of GI tract. IBS symptoms can include abdominal pain, changes in bowel movements such as diarrhea, constipation and alternating diarrhea/constipation, mucus in the stool, gassiness, abdominal bloating or the sensation of being full, abdominal distention or swelling, the urge to move bowel without being able to have a bowel movement, nausea, food intolerance, fatigue, and trouble sleeping. There are no complications of IBS. There is no definitive diagnostic test for IBS, review of symptoms and ruling out other diseases such as IBD, celiac disease and infections are used for diagnosis. Standard treatments for IBS include lifestyle changes, antidiarrheals, laxatives/stool softeners, antispasmodics, SSRIs, and probiotics.

4. Compounds for Treatment of GI Motility Disorders

Provided herein are methods for treating or reducing symptoms of a GI motility disorder using a compound of Formula I. Further, provided herein are methods for treating or reducing symptoms of a GI motility disorder that may include administering to a subject a therapeutically effective amount of a compound of Formula I, or a pharmaceutically acceptable salt thereof, or a composition comprising a compound of Formula I or its pharmaceutically acceptable salt.

"Isomerism" refers to compounds having the same atomic mass and atomic number but differing in one or more physical or chemical properties. Various types of isomerism include the following identified below.

"Stereoisomer" refers to a chemical compound having the same molecular weight, chemical composition, and constitution as another, but with the atoms grouped differently.

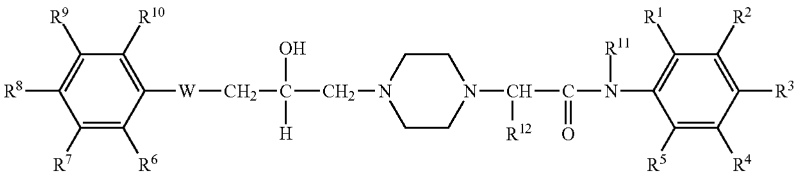
(I)

The compounds of Formula I are piperazine derivatives. The term "piperazine derivatives" is used interchangeably with the compounds of Formula I throughout. In some embodiments, $R^1$, $R^2$, $R^3$, $R^4$, and $R^5$ may each independently be a hydrogen, lower alkyl, lower alkoxy, cyano, trifluoromethyl, halo, lower alkylthio, lower alkyl sulfinyl, lower alkyl sulfonyl, or N-optionally substituted alkylamido (except that when $R^1$ is methyl, $R^4$ is not methyl); or $R^2$ and $R^3$ taken together form —$OCHO_2O$—. In some embodiments, $R^6$, $R^7$, $R^8$, $R^9$, and $R^{10}$ may each independently be a hydrogen, lower acyl, aminocarbonylmethyl, cyano, lower alkyl, lower alkoxy, trifluoromethyl, halo, lower alkylthio, lower alkyl sulfinyl, lower alkyl sulfonyl, di (lower alkyl) amino. In some embodiments, $R^6$ and $R^7$ together may form —CH=CH—CH=CH—. In some embodiments, $R^7$ and $R^8$ together may form —$OCH_2O$—. In some embodiments, $R^{11}$ and $R^{12}$ may each independently be a hydrogen or lower alkyl. In some embodiments, W may be an oxygen or sulfur. The methods may be used to alter contractility of GI tract muscles. In some embodiments, the methods as described above may decrease contractility of GI tract muscles. As used herein, "contractility" refers to any increase in the force of contraction that is not the result of the length-tension relationship observed in striated muscle, including for example skeletal muscle. Contractility includes muscles that possess the ability to self-contract or involuntarily contract, the capability of contracting (e.g. muscle fibers of shortening into a more compact form) without conscious effort and is automatically controlled by the nervous system.

"Aminocarbonylmethyl" refers to a group having the following structure:

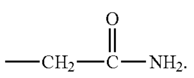

"Aryl" refers to an optionally substituted phenyl or naphthyl group where $R^6$ and $R^7$ together form —CH=CH—CH—CH—.

"Cyano" refers to a group having the following structure —C≡N.

"Di-lower alkyl amino" refers to a group having the following structure $R^{13}(R^{14})N$— wherein $R^{13}$ and $R^{14}$ are each independently lower alkyl as defined herein.

"Halo" or "halogen" refers to fluoro, chloro, bromo or iodo usually regarding halo substitution for a hydrogen atom in an organic compound.

That is, certain identical chemical moieties are at different orientations in space and, therefore, when pure, has the ability to rotate the plane of polarized light. However, some pure stereoisomers may have an optical rotation that is so slight that it is undetectable with present instrumentation.

"Optical isomerism" describes one type of stereoisomerism which manifests itself by the rotation that the isomer, either pure or in solution, imparts to the plane of polarized light. It is caused in many instances by the attachment of four different chemical atoms or groups to at least one of the carbon atoms in a molecule. These isomers may be described as d-, l-, or a d, l-pair or D-, L- or a D,L-pair; or R-, S-, or an R,S-pair, depending upon the nomenclature system employed.

"Diastereoisomer" refers to stereoisomers some or all of which are dissymmetric but which are not mirror images of each other. Diastereoisomers corresponding to a given structural formula must have at least two asymmetric atoms. A compound having two asymmetric atoms will usually exist in four diastereoisomeric forms, i.e. (−)-erythro, (+)-erythro, (−)-threo and (+)-threo.

In some embodiments, compounds of Formula I wherein $R^{12}$ is hydrogen may have one asymmetric carbon atom, i.e., the carbon atom 2 of the propyl moiety. These compounds may exist in two stereochemical forms; i.e., (+) and (−) or R and S, and mixtures thereof. In some embodiments, compounds of Formula I where $R^{12}$ is a group other than hydrogen may have two asymmetric carbon atoms, i.e. the carbon atom at the 2 position of the propyl moiety, and the carbon atom to which $R^{12}$ is attached. These compounds may exist in four stereochemical forms (+)-erythro-, (−)-erythro-, (+)-threo-, (−)-threo and mixtures thereof. The Cahn-Prelog convention will describe these four isomers as R—R, R—S, S—R, and S—S, which denotes the stereochemistry at each of the asymmetric carbon atoms. The R and S designation will be used in this application. This patent application is to be interpreted to include the individual stereoisomers as well as mixtures thereof.

Individual stereoisomers of compounds described may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii)

separation of the mixture of enantiomers or diastereomers on chiral chromatographic columns.

"Structure of Formula I" refers to the generic structure of the compounds detailed herein.

"Lower acyl" refers to a group having the following structure:

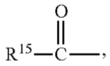

wherein $R^{15}$ is a lower alkyl as is defined herein, and includes such groups as acetyl, propanoyl, n-butanoyl and the like.

"Lower alkyl" refers to an unbranched saturated hydrocarbon chain of 1-4 carbons, such as, for example, methyl, ethyl, n-propyl, and n-butyl.

"Lower alkoxy" refers to a group-OR wherein R is lower alkyl as herein defined.

"Lower alkylthio" refers to a group —SR wherein R is lower alkyl as herein defined.

"Lower alkyl sulfinyl" refers to:

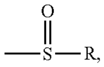

wherein R is lower alkyl as herein defined.

"Lower alkyl sulfonyl" refers to:

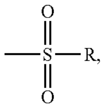

wherein R is lower alkyl as herein defined.

"N-Optionally substituted alkylamido" refers to a group having the following structure:

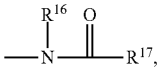

wherein $R^{16}$ is independently hydrogen or lower alkyl and $R^{17}$ is lower alkyl as defined herein.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described, and may include those processes wherein the free base is converted to the acid addition salt and those processes in which it is not.

As used herein, the terms "salt" or "salts" refer to an acid addition or base addition salt of a compound of the disclosure. "Salts" include in particular "pharmaceutical acceptable salts." The term "pharmaceutically acceptable salts" refers to salts that retain the biological effectiveness and properties of the compounds of this disclosure and, which typically are not biologically or otherwise undesirable. In many cases, the compounds of the present disclosure are capable of forming acid and/or base salts by virtue of the presence of amino and/or carboxyl groups or groups similar thereto.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. Pharmaceutically acceptable acid addition salts can be formed with inorganic acids and organic acids. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present disclosure provides compounds of Formula I in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

"Pharmaceutically acceptable ester" of the compound of Formula I which may be used in therapy includes those containing the alkanoyloxy group, —O—C(═O)—Z, wherein Z is an alkyl group containing 1 to 12 carbon atoms, which is attached to carbon atom 2 of the propylene linkage instead of the hydroxyl group, i.e., the hydroxy group has been esterified. The group, Z, may be for example, methyl, ethyl, butyl, hexyl, octyl, dodecyl and the like. This disclosure contemplates those compounds of Formula I which are esters as described herein and at the same time are the pharmaceutically acceptable acid addition salts thereof.

"Piperazino" structure describes the following saturated six-membered dinitrogen substituted heterocyclic moiety:

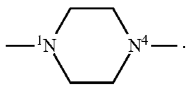

The locations for the substituents on the ring system of the above compounds of the instant disclosure are as depicted in Formula I. For example, in some embodiments, when $R^1$ and $R^5$ are methyl, $R^6$ is methoxy, $R^2$ to $R^4$ and $R^7$ to $R^{12}$ are hydrogen, and Wis oxygen, the compound of Formula I may be 1-[3-(2-methoxyphenoxy-2-hydroxypropyl]-4-[(2,6-dimethylphenyl)aminocarbonylmethyl]piperazine (Formula II):

(II)

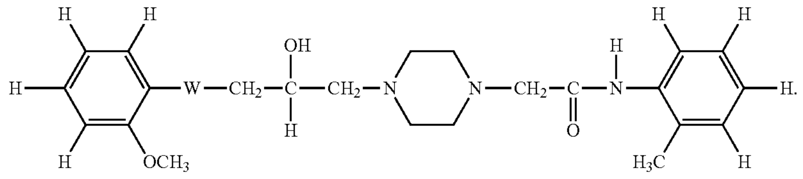

This compound may also be named as N-(2,6-dimethylphenyl)-2-(4-(2-hydroxy-3-(2-methoxyphenoxy)propyl) piperazin-1-yl)acetamide. U.S. Pat. No. 4,567,264 is fully incorporated herein by reference.

a. Ranolazine

Ranolazine is a piperazine derivative, sold under the trade name Ranexa® by Gilead Sciences, received FDA approval in 2006 for chronic angina. Ranexa® is available as a film-coated, non-scored, extended-release tablet for oral administration. Ranolazine is a racemic mixture of enantiomeric forms, S-ranolazine and R-ranolazine, chemically described as 1-piperazineacetamide, N-(2,6-dimethylphenyl)-4-[2-hydroxy-3-(2-methoxyphenoxy) propyl]-, (±)-. It has an empirical formula of $C_{24}H_{33}N_3O_4$ and a molecular weight of 427.54 g/mole.

Ranolazine is rapidly metabolized through the cytochrome P-450 3A enzyme (CYP3A) pathway in the liver. Ranolazine is also metabolized in the intestine. At least 70% of ingested ranolazine is excreted in the urine. Ranolazine blocks/inhibits persistent or late inward sodium current in various voltage-gated sodium channels. Specifically, ranolazine is an inhibitor of the cardiac late sodium current (late $I_{Na}$), which is the residual $Na^+$ flowing after the large peak (peak $I_{Na}$) during an action potential. Although the late $I_{Na}$ is relatively small under normal conditions, the overall flow of $Na^+$ loading is greater during the brief peak $I_{Na}$. This sodium overload promotes an increased exchange of intracellular $Na^+$ for extracellular calcium ($Ca^{2+}$), causing $Ca^{2+}$ overload and prolongation of the action potential. Increased late $I_{Na}$ is thought to involve a fundamental change or defect in the inactivation gate in a select population of channels and has been implicated in the pathogenesis of human cardiac conditions. Ranolazine is structurally similar to lidocaine (LA) and other LA molecules, and mutational experiments have indicated that ranolazine binds to the same LA receptor which faces the inner pore region of the channel within domains III and IV, which is also where the inactivation gate is located. Ranolazine has been shown to have a nine-fold selectively for late $I_{Na}$ vs peak $I_{Na}$. Ranolazine has also been shown to block KCNH2-encoded hERG K+ channels that are found in both cardiac muscle and intestinal smooth muscle. Inhibition of persistent or late inward sodium current leads to reductions in intracellular calcium levels. Ranolazine prolongs the action potential duration and blocks the persistent or late inward sodium currents and prevents calcium overload. Ranolazine stabilizes membranes and reduces excitability of neurons. Ranolazine blocks both peak amplitude and mechanosensitivity of sodium current in human colon SMCs and decreases contractility of human colon muscle strips.

In some embodiments, Formula I or Formula II compounds or compositions as detailed herein, or at least one component thereof, may inhibit the late sodium current of an action potential in GI system cells, such as intestinal SMCs, motor neurons, sensory neurons, fibroblasts, ICC, epithelial cells, goblet cells, or combinations thereof. In some embodiments, Formula I or Formula II compounds or compositions as detailed herein, or at least one component thereof, may reduce intracellular sodium in GI system cells. In some embodiments, Formula I or Formula II compounds or compositions as detailed herein, or at least one component thereof, may reduce intracellular calcium in GI system cells. In some embodiments, Formula I or Formula II compounds or compositions as detailed herein, or at least one component thereof, may restore intracellular ion homeostasis in GI system cells.

Ranolazine is currently under investigation for cardiovascular disease (CVD)- and diabetes-related indications. In some embodiments, the FDA-approved doses of ranolazine for chronic angina, 500 mg twice daily and 1000 mg twice daily, may be used. In some embodiments, Formula I compounds described herein or Formula II compounds may be administered at about 100 mg twice daily, about 200 mg twice daily, about 300 mg twice daily, about 400 mg twice daily, about 500 mg twice daily, about 600 mg twice daily, about 700 mg twice daily, about 800 mg twice daily, about 900 mg twice daily, about 1000 mg twice daily, about 1100 mg twice daily, about 1200 mg twice daily, about 1300 mg twice daily, about 1400 mg twice daily, about 1500 mg twice daily, about 1600 mg twice daily, about 1700 mg twice daily, about 1800 mg twice daily, about 1900 mg twice daily, or about 2000 mg twice daily. In some embodiments, Formula I compounds described herein or Formula II compounds may be administered at, at least 100 mg twice daily, at least 200 mg twice daily, at least 300 mg twice daily, at least 400 mg twice daily, at least 500 mg twice daily, at least 600 mg twice daily, at least 700 mg twice daily, at least 800 mg twice daily, at least 900 mg twice daily, at least 1000 mg twice daily, at least 1100 mg twice daily, at least 1200 mg twice daily, at least 1300 mg twice daily, at least 1400 mg twice daily, at least 1500 mg twice daily, at least 1600 mg twice daily, at least 1700 mg twice daily, at least 1800 mg twice daily, or at least 1900 mg twice daily. In some embodiments, Formula I compounds described herein or Formula II compounds may be administered at, at most 2000 mg twice daily, at most 1900 mg twice daily, at most 1800 mg twice daily, at most 1700 mg twice daily, at most 1600 mg twice daily, at most 1500 mg twice daily, at most 1400 mg twice daily, at most 1300 mg twice daily, at most 1200 mg twice daily, at most 1100 mg twice daily, at most 1000 mg twice daily, at most 900 mg twice daily, at most 800 mg twice daily, at most 700 mg twice daily, at most 600 mg twice daily, at most 500 mg twice daily, at most 400 mg twice daily, at most 300 mg twice daily, or at most 200 mg twice daily. Formula I compounds described herein or Formula II compounds may typically be administered from about 100 mg to about 2000 mg twice daily.

The daily dosage of Formula I compounds described herein or Formula II compounds may be about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg. In some embodiments, the daily dosage of Formula I compounds described herein or Formula II compounds may be at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, at least 1400 mg, at least 1500 mg, at least 1600 mg, at least 1700 mg, at least 1800 mg, or at least 1900 mg. In some embodiments, the daily dosage of Formula I compounds described herein or Formula II compounds may be at most 2000 mg, at most 1900 mg, at most 1800 mg, at most 1700 mg, at most 1600 mg, at most 1500 mg, at most 1400 mg, at most 1300 mg, at most 1200 mg, at most 1100 mg, at most 1000 mg, at most 900 mg, at most 800 mg, at most 700 mg, at most 600 mg, at most 500 mg, at most 400 mg, at most 300 mg, or at most 200 mg. The daily dosage of Formula I compounds described herein or Formula II compounds may typically be from about 100 mg to about 2000 mg.

Formula I compounds described herein or Formula II compounds may be dispensed as 50 mg oral tablets, 100 mg oral tablets, 150 mg oral tablets, 200 mg oral tablets, 250 mg oral tablets, 300 mg oral tablets, 350 mg oral tablets, 400 mg oral tablets, 450 mg oral tablets, 500 mg oral tablets, 550 mg oral tablets, 600 mg oral tablets, 650 mg oral tablets, 700 mg oral tablets, 750 mg oral tablets, 800 mg oral tablets, 850 mg oral tablets, 900 mg oral tablets, 950 mg oral tablets, 1000 mg oral tablets. In some embodiments, Formula I compounds described herein or Formula II compounds may be dispensed as 500 mg oral tablets. When used properly and not concurrently with contraindicated drugs, a compound of Formula II has been shown to be safe and well-tolerated. The most common side effects include dizziness, nausea, constipation, and headache; less than 2% of patients experience these side effects.

Specific components of GI contractility could be affected by Formula I compounds described herein or Formula II compounds. In some embodiments, Formula I compounds described herein or Formula II compounds may synchronize contractile activity across the GI tract. In some embodiments, Formula I compounds described herein or Formula II compounds may induce adequate timing of contractile activity, such as for water to be absorbed. In some embodiments, Formula I compounds described herein or Formula II compounds may generate high amplitude propagating contractions that are the right frequency. In some embodiments, Formula I compounds described herein or Formula II compounds may produce peristaltic waves in one-way direction. In some embodiments, Formula I compounds described herein or Formula II compounds may restore pressure in the gut wall biomechanical functions to homeostasis. In some embodiments, Formula I compounds described herein or Formula II compounds may reduce clinical presentation of motility issues.

In some embodiments, Formula I compounds described herein or Formula II compounds may decrease frequency of stools. In some embodiments, Formula I compounds described herein or Formula II compounds may improve the consistency of stools, such as decreasing loose and watery stools. As used herein, "loose stool" refers to Bristol stool chart types 5-7. The Bristol stool chart classifies feces into seven groups/types based on the appearance of the feces. The seven types are: type 1 is feces that separates into hard lumps, like nuts, and can be difficult to pass and black in color; type 2 is feces that is sausage-shaped and lumpy; type 3 is like a sausage and has cracks on the surface (can be black in color); type 4 is like a sausage or snake and is smooth and soft-it is considered to be an average stool; type 5 is soft blobs with clear cut edges; type 6 is fluffy pieces with ragged edges and is mushy-it is considered to be diarrhea; type 7 is watery with no solid pieces and is entirely liquid, it is also considered to be diarrhea. Types 1 and 2 indicate constipation, types 3 and 4 are ideal stools that are easy to defecate and do not contain excess liquid, type 5 is tending towards diarrhea, and types 6 and 7 indicate diarrhea.

In some embodiments, Formula I compounds described herein or Formula II compounds may reduce the subjective sense of urgency. In some embodiments, Formula I compounds described herein or Formula II compounds may reduce bloating. In some embodiments, Formula I compounds described herein or Formula II compounds may reduce abdominal cramping. In some embodiments, Formula I compounds described herein or Formula II compounds may reduce pain, such as abdominal or GI pain. In some embodiments, Formula I compounds described herein or Formula II compounds may have anti-inflammatory effects. In some embodiments, the anti-inflammatory effects of Formula I compounds described herein or Formula II compounds may be caused by restoring motility to homeostasis and decreasing diarrhea. In some embodiments, Formula I compounds described herein or Formula II compounds may restore temporal and spatial coordination of intestinal smooth muscle contractions and relaxations.

Formula I compounds described herein or Formula II compounds may have an effect on inflammatory biomarkers. In some embodiments, Formula I compounds described herein or Formula II compounds may attenuate pro-inflammatory cytokines such as IL-1$\alpha$, IL-1$\beta$, IL-6, and TNF-$\alpha$. In some embodiments, Formula I compounds described herein or Formula II compounds may decrease the pro-inflammatory cytokines IL-1$\beta$ and TNF-$\alpha$. In some embodiments, Formula I compounds described herein or Formula II compounds may increase anti-inflammatory PPAR-y expression. In some embodiments, Formula I compounds described herein or Formula II compounds may increase myogenesis. In some embodiments, Formula 1 compounds described herein or Formula II compounds may reduce a pro-oxidant inflammation/oxidative condition. In some embodiments, Formula I compounds described herein or Formula II compounds may have anti-inflammatory effects. In some embodiments, Formula I compounds described herein or Formula II compounds may reduce C reactive protein. In some embodiments, Formula I compounds described herein or Formula II compounds may reduce asymmetric dimethylarginine.

5. Pharmaceutical Compositions

Further provided herein are pharmaceutical compositions comprising the above-described Formula I or Formula II compounds or pharmaceutically acceptable salts thereof. In some embodiments, the composition may include about 100 mg to about 2000 mg, about 200 mg to about 1900 mg, about 300 mg to about 1800 mg, about 400 mg to about 1700 mg, about 500 mg to about 1600 mg, about 600 mg to about 1500 mg, about 700 mg to about 1400 mg, about 800 mg to about 1300 mg, about 900 mg to about 1200 mg, about 1000 mg to about 1100 mg, about 1100 mg to about 1000 mg, about 1200 mg to about 900 mg, about 1300 mg to about 800 mg, about 1400 mg to about 700 mg, about 1500 mg to about 600 mg, about 1600 mg to about 500 mg, about 1700 mg to about 400 mg, about 1800 mg to about 300 mg, about 1900 mg to about 200 mg, or about 2000 mg to about 100 mg of a compound described herein. In some embodiments, the composition may include about 400 mg to about 1000 mg, about 410 mg to about 1000 mg, about 420 mg to about 1000 mg, about 430 mg to about 1000 mg, about 440 mg to about 1000 mg, about 450 mg to about 1000 mg, about 460 mg to about 1000 mg, about 470 mg to about 1000 mg, about 480 mg to about 1000 mg, about 490 mg to about 1000 mg, about 500 mg to about 1000 mg, about 510 mg to about 1000 mg, about 520 mg to about 1000 mg, about 530 mg to about 1000 mg, about 540 mg to about 1000 mg, about 550 mg to about 1000 mg, about 560 mg to about 1000 mg, about 570 mg to about 1000 mg, about 580 mg to about 1000 mg, about 590 mg to about 1000 mg, or about 600 mg to about 1000 mg of a compound described herein. In some embodiments, the composition may include about 500 mg to about 990 mg, about 500 mg to about 980 mg, about 500 mg to about 970 mg, about 500 mg to about 960 mg, about 500 mg to about 950 mg, about 500 mg to about 940 mg, about 500 mg to about 930 mg, about 500 mg to about 920 mg, about 500 mg to about 910 mg, about 500 mg to about 900 mg, about 500 mg to about 890 mg, about 500 mg to about 880 mg, about 500 mg to about 870 mg, about 500 mg to about 860 mg, about 500 mg to about 850 mg, about 500 mg to about 840 mg, about 500 mg to about 830 mg, about 500 mg to about 820 mg, about 500 mg to about 810 mg, about 500 mg to about 800 mg, about 500 mg to about 790 mg, about 500 mg to about 780 mg, about 500 mg to about 770 mg, about 500 mg to about 760 mg, about 500 mg to about 750 mg, about 500 mg to about 740 mg, about 500 mg to about 730 mg, about 500 mg to about 720 mg, about 500 mg to about 710 mg, about 500 mg to about 700 mg, about 500 mg to about 690 mg, about 500 mg to about 680 mg, about 500 mg to about 670 mg, about 500 mg to about 660 mg, about 500 mg to about 650 mg, about 500 mg to about 640 mg, about 500 mg to about 630 mg, about 500 mg to about 620 mg, about 500 mg to about 610 mg, about 500 mg to about 600 mg, about 500 mg to about 590 mg, about 500 mg to about 580 mg, about 500 mg to about 570 mg, about 500 mg to about 560 mg, about 500 mg to about 550 mg of a compound described herein.

In some embodiments, the composition may include at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, at least 240 mg, at least 250 mg, at least 260 mg, at least 270 mg, at least 280 mg, at least 290 mg, at least 300 mg, at least 310 mg, at least 320 mg, at least 330 mg, at least 340 mg, at least 350 mg, at least 360 mg, at least 370 mg, at least 380 mg, at least 390 mg, at least 400 mg, at least 410 mg, at least 420 mg, at least 430 mg, at least 440 mg, at least 450 mg, at least 460 mg, at least 470 mg, at least 480 mg, at least 490 mg, at least 500 mg, at least 510 mg, at least 520 mg, at least 530 mg, at least 540 mg, at least 550 mg, at least 560 mg, at least 570 mg, at least 580 mg, at least 590 mg, at least 600 mg, at least 610 mg, at least 620 mg, at least 630 mg, at least 640 mg, at least 650 mg, at least 660 mg, at least 670 mg, at least 680 mg, at least 690 mg, at least 700 mg, at least 710 mg, at least 720 mg, at least 730 mg, at least 740 mg, at least 750 mg, at least 760 mg, at least 770 mg, at least 780 mg, at least 790 mg, at least 800 mg, at least 810 mg, at least 820 mg, at least 830 mg, at least 840 mg, at least 850 mg, at least 860 mg, at least 870 mg, at least 880 mg, at least 890 mg, at least 900 mg, at least 910 mg, at least 920 mg, at least 930 mg, at least 940 mg, at least 950 mg, at least 960 mg, at least 970 mg, at least 980 mg, at least 990 mg, at least 1000 mg, at least 1010 mg, at least 1020 mg, at least 1030 mg, at least 1040 mg, at least 1050 mg, at least 1060 mg, at least 1070 mg, at least 1080 mg, at least 1090 mg, at least 1100 mg, at least 1110 mg, at least 1120 mg, at least 1130 mg, at least 1140 mg, at least 1150 mg, at least 1160 mg, at least 1170 mg, at least 1180 mg, at least 1190 mg, at least 1200 mg, at least 1210 mg, at least 1220 mg, at least 1230 mg, at least 1240 mg, at least 1250 mg, at least 1260 mg, at least 1270 mg, at least 1280 mg, at least 1290 mg, at least 1300 mg, at least 1310 mg, at least 1320 mg, at least 1330 mg, at least 1340 mg, at least 1350 mg, at least 1360 mg, at least 1370 mg, at least 1380 mg, at least 1390 mg, at least 1400 mg, at least 1410 mg, at least 1420 mg, at least 1430 mg, at least 1440 mg, at least 1450 mg, at least 1460 mg, at least 1470 mg, at least 1480 mg, at least 1490 mg, at least 1500 mg, at least 1510 mg, at least 1520 mg, at least 1530 mg, at least 1540 mg, at least 1550 mg, at least 1560 mg, at least 1570 mg, at least 1580 mg, at least 1590 mg, at least 1600 mg, at least 1610 mg, at least 1620 mg, at least 1630 mg, at least 1640 mg, at least 1650 mg, at least 1660 mg, at least 1670 mg, at least 1680 mg, at least 1690 mg, at least 1700 mg, at least 1710 mg, at least 1720 mg, at least 1730 mg, at least 1740 mg, at least 1750 mg, at least 1760 mg, at least 1770 mg, at least 1780 mg, at least 1790 mg, at least 1800 mg, at least 1810 mg, at least 1820 mg, at least 1830 mg, at least 1840 mg, at least 1850 mg, at least 1860 mg, at least 1870 mg, at least 1880 mg, at least 1890 mg, at least 1900 mg, at least 1910 mg, at least 1920 mg, at least 1930 mg, at least 1940 mg, at least 1950 mg, at least 1960 mg, at least 1970 mg, at least 1980 mg, or at least 1990 mg of a compound described herein.

In some embodiments, the composition may include less than 2000 mg, less than 1990 mg, less than 1980 mg, less than 1970 mg, less than 1960 mg, less than 1950 mg, less than 1940 mg, less than 1930 mg, less than 1920 mg, less than 1910 mg, less than 1900 mg, less than 1890 mg, less than 1880 mg, less than 1870 mg, less than 1860 mg, less than 1850 mg, less than 1840 mg, less than 1830 mg, less than 1820 mg, less than 1810 mg, less than 1800 mg, less than 1790 mg, less than 1780 mg, less than 1770 mg, less than 1760 mg, less than 1750 mg, less than 1740 mg, less than 1730 mg, less than 1720 mg, less than 1710 mg, less than 1700 mg, less than 1690 mg, less than 1680 mg, less than 1670 mg, less than 1660 mg, less than 1650 mg, less than 1640 mg, less than 1630 mg, less than 1620 mg, less than 1610 mg, less than 1600 mg, less than 1590 mg, less than 1580 mg, less than 1570 mg, less than 1560 mg, less than 1550 mg, less than 1540 mg, less than 1530 mg, less than 1520 mg, less than 1510 mg, less than 1500 mg, less than 1490 mg, less than 1480 mg, less than 1470 mg, less than 1460 mg, less than 1450 mg, less than 1440 mg, less than 1430 mg, less than 1420 mg, less than 1410 mg, less than 1400 mg, less than 1390 mg, less than 1380 mg, less than 1370 mg, less than 1360 mg, less than 1350 mg, less than 1340 mg, less than 1330 mg, less than 1320 mg, less than 1310 mg, less than 1300 mg, less than 1290 mg, less than 1280 mg, less than 1270 mg, less than 1260 mg, less than 1250 mg, less than 1240 mg, less than 1230 mg, less than 1220 mg, less than 1210 mg, less than 1200 mg, less than 1190 mg, less than 1180 mg, less than 1170 mg, less than 1160 mg, less than 1150 mg, less than 1140 mg, less than 1130 mg, less than 1120 mg, less than 1110 mg, less than 1100 mg, less than 1090 mg, less than 1080 mg, less than 1070 mg, less than 1060 mg, less than 1050 mg, less than 1040 mg, less than 1030 mg, less than 1020 mg, less than 1010 mg, less than 1000 mg, less than 990 mg, less than 980 mg, less than 970 mg, less than 960 mg, less than 950 mg, less than 940 mg, less than 930 mg, less than 920 mg, less than 910 mg, less than 900 mg, less than 890 mg, less than 880 mg, less than 870 mg, less than 860 mg, less than 850 mg, less than 840 mg, less than 830 mg, less than 820 mg, less than 810 mg, less than 800 mg, less than 790 mg, less than 780 mg, less than 770 mg, less than 760 mg, less than 750 mg, less than 740 mg, less than 730 mg, less than 720 mg, less than 710 mg, less than 700 mg, less than 690 mg, less than 680 mg, less than 670 mg, less than 660 mg, less than 650 mg, less than 640 mg, less than 630 mg, less than 620 mg, less than 610 mg, less than 600 mg, less than 590 mg, less than 580 mg, less than 570 mg, less than 560 mg, less than 550 mg, less than 540 mg, less than 530 mg, less than 520 mg, less than 510 mg, less than 500 mg, less than 490 mg, less than 480 mg, less than 470 mg, less than 460 mg, less than 450 mg, less than 440 mg, less than 430 mg, less than 420 mg, less than 410 mg, less than 400 mg, less than 390 mg, less than 380 mg, less than 370 mg, less than 360 mg, less than 350 mg, less than 340 mg, less than 330 mg, less than 320 mg, less than 310 mg, less than 300 mg, less than 290 mg, less than 280 mg, less than 270 mg, less than 260 mg, less than 250 mg, less than 240 mg, less than 230 mg, less than 220 mg, less than 210 mg, less than 200 mg, less than 190 mg, less than 180 mg, less than 170 mg, less than 160 mg, less than 150 mg, less than 140 mg, less than 130 mg, less than 120 mg, or less than 110 mg of a compound described herein.

In some embodiments, the composition may include about 500 mg to about 1000 mg of a compound described herein.

Formula I compounds or Formula II compounds or pharmaceutically acceptable salts thereof as detailed herein, or at least one component thereof, may be formulated into pharmaceutical compositions in accordance with standard techniques well known to those skilled in the pharmaceutical art. The pharmaceutical compositions can be formulated according to the mode of administration to be used. In cases where pharmaceutical compositions are injectable pharmaceutical compositions, they are sterile, pyrogen free, and particulate free. An isotonic formulation is in some embodiments used. Generally, additives for isotonicity may include sodium chloride, dextrose, mannitol, sorbitol and lactose. In some cases, isotonic solutions such as phosphate buffered saline can be used. Stabilizers include gelatin and albumin. In some embodiments, a secondary treatment for CD is added to the composition. In some embodiments, anti-inflammatoiremmunosuppressants, antibiotics, analgesics, iron supplements, vitamin B-12 shots, calcium supplements, vitamin D supplements, or combinations thereof are added to the composition. In some embodiments, proton-pump inhibitors or H2-receptor blockers, or combinations thereof are added to the composition. Anti-inflammatories may include one or more of the following: corticosteroids, 5-aminosalicylates, mesalamine (Asacol HD, Delzicol, etc.), balsalazide (Colazal), olsalazine (Dipentum). Immunosuppressants may include corticosteroids, such as, but not limited to, methylprednisolone, hydrocortisone, prednisone, prednisolone, budesonide, and dexamethasone. Immunosuppressants may include one or more of the following: Azathioprine, Infliximab, Methotrexate, Natalizumab, Vedolizumab, Ustekinumab, 6-mercaptopurine (6-MP). Antibiotics may include metronidazole or ciprofloxacin. Analgesics may include one or more of the following: opioids (narcotics), such as Avinza, Kadian, MS Contin (morphine), Oxycontin (oxycodone), Dolophine or Methadose (methadone), Dilaudid (hydromorphone), codeine, Demerol (meperidine), Duragesic or Actiq (fentanyl); Tylenol (acetaminophen); non-steroidal anti-inflammatory drugs (NSAIDs), such as Advil (ibuprofen), Aleve (naproxen), Celebrex (celecoxib), Aspirin (acetylsalicylic acid).

The composition may further comprise a pharmaceutically acceptable excipient. The pharmaceutically acceptable excipient may be functional molecules as vehicles, adjuvants, carriers, or diluents. The term "pharmaceutically acceptable carrier," may be a non-toxic, inert solid, semi-solid or liquid filler, diluent, encapsulating material or formulation auxiliary of any type. Pharmaceutically acceptable carriers include, for example, diluents, lubricants, binders, disintegrants, colorants, flavors, sweeteners, antioxidants, preservatives, glidants, solvents, suspending agents, wetting agents, surfactants, emollients, propellants, humectants, powders, pH adjusting agents, and combinations thereof. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents. The transfection facilitating agent may be a polyanion, polycation, including poly-L-glutamate (LGS), or lipid.

In another aspect, the present disclosure provides a pharmaceutical composition comprising a compound as described herein, or a pharmaceutically acceptable salt thereof, and a pharmaceutically acceptable carrier. In a further embodiment, the composition comprises at least two pharmaceutically acceptable carriers, such as those described herein. For purposes of the present disclosure, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present disclosure can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. In some embodiments, the pharmaceutical compositions are tablets or gelatin capsules comprising the active ingredient together with one or more of: diluents, e.g., lactose, dextrose, sucrose, mannitol, sorbitol, cellulose and/or glycine; lubricants, e.g., silica, talcum, stearic acid, its magnesium or calcium salt and/or polyethyleneglycol; binders, e.g., magnesium aluminum silicate, starch paste, gelatin, tragacanth, methylcellulose, sodium carboxymethylcellulose and/or polyvinylpyrrolidone; disintegrants, e.g., starches, agar, alginic acid or its sodium salt, or effervescent mixtures; and absorbents, colorants, flavors and sweeteners.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions may be prepared according to conventional mixing, granulating or coating methods, respectively, and contain about 0.1-100%, or about 0.1-75%, or contain about 1-50%, of the active ingredient.

6. Administration

The compounds of Formula I, piperazine derivatives or Formula II compounds or pharmaceutically acceptable salts thereof as detailed herein, or at least one component thereof, may be administered or delivered to a subject or a cell of the subject. Formula I or Formula II compounds or pharmaceutically acceptable salts thereof as detailed herein, or at least one component thereof, may be administered or delivered to a subject or a cell of the subject in a therapeutically effective amount. Such compositions can be administered in dosages and by techniques well known to those skilled in the medical arts taking into consideration such factors as the age, sex, weight, and condition of the particular subject, and the route of administration. The presently disclosed Formula I or Formula II compounds or pharmaceutically acceptable salts thereof, or compositions comprising the same, may be administered to a subject by different routes including orally, parenterally, sublingually, transdermally, rectally, transmucosally, topically, intranasal, intravaginal, via inhalation, via buccal administration, intrapleurally, intravenous, intraarterial, intraperitoneal, subcutaneous, intradermally, epidermally, intramuscular, intranasal, intrathecal, intracranial, and intraarticular or combinations thereof.

The term "a therapeutically effective amount" of a compound as described herein refers to an amount of the compound as described herein that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of as described herein that, when administered to a subject, is effective to (1) at least partially alleviate, inhibit, prevent and/or ameliorate a condition, or a disorder or a disease (i) mediated by GI dysmotility, or (ii) associated with sodium channel activity, or (iii) characterized by activity (normal or abnormal) of sodium channels; or (2) reduce or inhibit the activity of sodium channels; or (3) reduce or inhibit the expression of sodium channels. In another non-limiting embodiment, the term "a therapeutically effective amount" refers to the amount of the compound of the present disclosure that, when administered to a cell, or a tissue, or a non-cellular biological material, or a medium, is effective to at least partially reducing or inhibiting the activity of sodium channels; or at least partially reducing or inhibiting the expression of sodium channels. The meaning of the term "a therapeutically effective amount" as illustrated in the above embodiments for GI motility disorders and sodium channels also applies by the same means to any other relevant disorders or conditions or proteins/peptides/enzymes associated with the disorders, such as diarrhea not caused by a GI motility disorder, or other voltage-gated sodium channel dysfunction disorders, and the like.

In some embodiments, the compositions or compounds described herein may be administered concomitantly with a secondary treatment for CD. In some embodiments, the compositions or compounds described herein may be administered once per day, twice per day, or three times per day. In some embodiments, the compositions or compounds described herein may be administered to the subject more than once per day. In some embodiments, the compositions or compounds described herein may be administered about 3 hours to about 12 hours apart, about 4 hours to about 12 hours apart, about 5 hours to about 12 hours apart, about 6 hours to about 12 hours apart, about 7 hours to about 12 hours apart, about 8 hours to about 12 hours apart, about 9 hours to about 12 hours apart, or about 10 hours to about 12 hours apart. In some embodiments, the compositions or compounds described herein may be administered at least 3 hours apart, at least 4 hours apart, at least 5 hours apart, at least 6 hours apart, at least 7 hours apart, at least 8 hours apart, at least 9 hours apart, at least 10 hours apart, or at least 11 hours apart. In some embodiments, the compositions or compounds described herein may be administered at most 12 hours apart, at most 11 hours apart, at most 10 hours apart, at most 9 hours apart, at most 8 hours apart, at most 7 hours apart, at most 6 hours apart, at most 5 hours apart, or at most 4 hours apart. In some embodiments, the compositions or compounds described herein may be administered once in the morning and once in the evening. In some embodiments, the compositions or compounds described herein may be administered without food or with food. In some embodiments, the compositions or compounds described herein may be administered about 0 minutes, about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 120 minutes, or about 150 minutes prior to food consumption. In some embodiments, the compositions or compounds described herein may be administered at least 0 minutes, at least 5 minutes, at least 10 minutes, at least 15 minutes, at least 20 minutes, at least 25 minutes, at least 30 minutes, at least 35 minutes, at least 40 minutes, at least 45 minutes, at least 50 minutes, at least 55 minutes, at least 60 minutes, or at least 120 minutes prior to food consumption. In some embodiments, the compositions or compounds described herein may be administered at most 150 minutes, at most 60 minutes, at most 55 minutes, at most 50 minutes, at most 45 minutes, at most 40 minutes, at most 35 minutes, at most 30 minutes, at most 25 minutes, at most 20 minutes, at most 15 minutes, at most 10 minutes, or at most 5 minutes prior to food consumption. The compositions or compounds described herein may typically be administered about 0 minutes to about 150 minutes prior to food consumption.

Following delivery of the presently disclosed Formula I or Formula II compounds or pharmaceutically acceptable salts thereof, or compositions comprising the same, and thereupon delivery of the active ingredient as described herein into the cells of the subject, the cells may have decreased intracellular sodium. Following administration of the presently disclosed Formula I or Formula II compounds or pharmaceutically acceptable salts thereof, or compositions comprising the same to a subject, the subject may have the number of loose stools is reduced by at least 5%, at least 10%, at least 15%, at least 20%, at least 25%, at least 30%, at least 35%, at least 40%, at least 45%, or at least 50%. The subject may exhibit ≥2, ≥3, ≥4, ≥5, or ≥6 loose stools per day on average before administration of the composition or compound. The subject may not be constipated before administration of the composition or compound. Following administration of the presently disclosed Formula I or Formula II compounds or pharmaceutically acceptable salts thereof, or compositions comprising the same to a subject, emotional disorders in the subject may be reduced. The emotional disorders can include anxiety, depression, anhedonia, antisocial disorder, and/or agoraphobia.

a. Cell Types

Any of the delivery methods and/or routes of administration detailed herein can be utilized with a myriad of cell types, for example, those cell types currently under investigation for GI motility disorders, including, but not limited to, ICC, intestinal SMCs, sensory neurons, neurons of the brain-gut axis, neurons of the autonomic nervous system, neurons of the enteric nervous system, motor neurons, fibroblasts, epithelial cells, goblet cells, smooth muscle progenitors, skeletal muscle progenitors, human skeletal myoblasts, human smooth muscle myoblasts, or other myogenic progenitor cells. Cells can be modified in vivo or ex vivo.

7. Examples

The foregoing may be better understood by reference to the following examples, which are presented for purposes of illustration and are not intended to limit the scope of the invention. The present disclosure has multiple aspects and embodiments, illustrated by the appended non-limiting examples.

Example 1

PheWAS in Drug Repurposing and Discovery

SCN5A belongs to a family of genes responsible for making sodium channels. These channels play a major role in signaling the start of each heartbeat, coordinating heart chamber contractions, and maintaining a normal heart rhythm. Ranolazine is an antianginal medication that targets the sodium channel subunit encoded by SCN5A. A phenome-wide association study (PheWAS) was conducted and it was found that there are strong anchoring cardiac phenotypes and also a novel UC association. Upon review of patient charts, it became clear that these patients were miscoded for UC and were actually diagnosed with CD.

PheWAS is a method that explores the association between single nucleotide polymorphisms (SNPs) and diseases across the human phenome. This approach has been used to identify phenotypes associated with SNPs in various genes, including those producing proteins selectively targeted by FDA approved drugs. PheWAS leverages Vanderbilt's informatics and data mining expertise combined with robust de-identified health records with associated genomic data in BioVU. The Exomechip contains >250,000 coding variants across the protein coding region of the human genome (as of May 2019). The coding variants were discovered through exome and whole genome sequencing in more than 12,000 individuals. It was designed to serve as an intermediate step between current genotyping arrays, which are designed to study common variants, and exome sequencing which can discover rare variants. Nearly all non-synonymous, splice and stop altering variants detected in an average genome through exome sequencing were included on the Exomechip. The Exomechip also includes single nucleotide polymorphisms (SNPs) with known disease associations as well as unpublished associations from consortia working on diabetes, blood lipids, blood pressure, lung function, myocardial infraction, anthropometric traits, psychiatric traits, Crohn's disease and age-related macular degeneration.

A PheWAS was performed in a disease-agnostic cohort of 28,000 BioVU patients in order to identify potential novel genotype-phenotype associations related to the SNPs in SCN5A. The effect of carrying at least one minor allele in this SNP on the presence of having various medical diagnoses (phenotypes) as defined by PheWAS codes derived from ICD-9 billing codes in the electronic health record (EHR) has been evaluated.

Using this precision drug repurposing method that leverages natural human genetic variation as a proxy for—and method of more accurately predicting—the physiologic effects of therapies in humans, ranolazine was identified as a possible new therapy for CD. A variant (P2006A) in the SCN5A gene, which encodes the sodium channel Nav1.5, significantly increases persistent sodium currents, functioning as a natural gain of function variant or 'agonist.' The SNP of interest in the current analysis of SCN5A mutations was a P2006A variant (TABLE 1). Sodium channels play a major role in signaling the start of each heartbeat, coordinating the contractions of the heart chambers, and maintaining a normal heart rhythm. A PheWAS uncovered a significant association between the P2006A variant and increased risk for heart palpitations (OR=4.2, P=0.0006), which was expected given ranolazine's known effects. Using this association as an 'anchor' in the dataset, phenotypes with a risk-causing OR >1 are possible new indications for ranolazine. PheWAS data showed a potential new indication for ranolazine for CD (OR=4.9, P=0.005).

TABLE 1

| SNP | rsID | Mutation | SIFT | PP2 | Exome MAF* | Variant Frequency | Populations with Highest MAF |
|---|---|---|---|---|---|---|---|
| P2006A | rs45489199 | | 0.9 | 0 | 0.00138 | 0.001911 | European (non-Finnish) |

*Minor allele frequency reflects the MAF in the BioVU Exomechip European ancestry population.

Sorting Intolerant from Tolerant (SIFT) scores at or below 0.05 are considered to be deleterious; those above 0.05 are considered to be tolerated. Polyphen2 (PP2) scores below 0.447 are considered benign; those higher than 0.908 are considered probably damaging; and those in between possibly damaging. The scores are coded to indicate benign or tolerated (normal font), possibly damaging (italic font) and probably damaging (underlined font).

Analysis of PheWAS results indicated a novel potential indication for use of ranolazine, UC (TABLE 2). Although the PheCODE is UC, this indication was further refined to CD after chart review revealed that this phenotype predominated in this case set (details in TABLE 3). This is prevalent in this therapeutic area: one study of early onset IBD showed that after a 12-year (1-22) follow-up, 57.9% of the diagnoses of all patients were modified.

TABLE 2

| Condition | PheWAS Code | rsID | SNP | p Value | Odds Ratio | Case Carriers | Total Cases |
|---|---|---|---|---|---|---|---|
| Ulcerative colitis | 555.2 | rs45489199 | — | 0.004616 | 4.9490 | 5 | 370 |

Chart reviews showed that these patients have IBD. Crohn's disease predominates (n=3); one additional patient had UC and one patient had an episode of acute colitis that did not persist as a chronic disease. Chart review details include: four out of five of the patients had true IBD, one patient was excluded with an acute episode of colitis that did not persist as a chronic issue; of the four patients with IBD only one was diagnosed with UC for which he had a total colectomy; there were a few instances where patients would be initially diagnosed with UC and then that diagnosis would be later changed to CD by their treating GI specialist, these diagnoses were typically changed after the colonoscopy showed some small bowel involvement that is only seen in CD; two patients' phenotypes included colonic CD; abdominal pain and bloody diarrhea were mentioned in charts of all three CD patients. Overview of patient charts are shown in TABLE 3.

TABLE 3

| | |
|---|---|
| Patient 1 | Small Bowel Crohn's-Multiple surgeries beg. in her early 20s involving small intestine removal-treated with lomotil. No colonic issues mentioned. Flare in 2007, 2012. Colonoscopy shows severe terminal illeum disease. |
| Patient 2 | Initially, Nonspecific colitis-treated with asacol, purinethol. After GI visit thought to be UC, but later changed to Crohn's after colonoscopy diagnosis favors "Crohn's disease primarily in the duodenum, colon and rectum." Biopsies: "showed normal terminal ileum, ascending and transverse colon showed eosinophils, descending colon showed acute colitis, and rectum showed acute inflammation which could be secondary to IBD." |
| Patient 3 | 1974: UC s/p total colectomy with ileostomy. No further IBD issues aside from ostomy follow-up. |
| Patient 4 | 2008 acute nonspecific colitis severe diverticulosis with bx COLON, SIGMOID, BIOPSY: FOCAL MINIMAL NONSPECIFIC ACUTE-COLITIS<br>Gastric bypass in 2016 with no mention of GI disease. |
| Patient 5 | 2009 Diagnosed with Ulcerative Colitis after a severe colitis flare involving proximal colon.<br>2009: Diagnosis was changed to Crohn's. Colonoscopy: severe changes of colitis most prominently in the cecum, ascending, transverse and descending colon. The sigmoid colon and rectum were significantly less inflamed-appearing with visible vasculature and scattered erosions/ulcers. worse on right side with some patchy inflammation and apthous ulcers on the left and rectal sparing. The features are more consistent with Crohn's colitis.<br>2012 Colonoscopy/biopsy: Right sided colonic disease. Postoperative Diagnosis: Normal terminal ileum and rectum. Colitis (558.9) found in the cecum and ascending colon. A pseudopolyp was found (556.4) in the transverse colon, descending colon, and sigmoid colon. |

TABLE 3-continued

Example 2

A Randomized, Double Blind, Placebo-Controlled, Crossover Study of Ranolazine for the Treatment of Crohn's Disease-Associated Diarrhea The hypothesis to be tested in this study is that sodium channel dysfunction may contribute to diarrhea among CD patients, and that inhibition of sodium currents may be beneficial. The overall goal is to conduct an exploratory clinical trial of the sodium channel blocker, ranolazine, in a population of CD patients who are experiencing persistent diarrhea. The study will use a crossover design. The crossover design was selected to yield a more efficient comparison of a treatment that aims to alleviate symptoms. Given the short, seven-hour half-life of ranolazine, the scientific value of adding an extra study visit to account for a 1.5-day to 3-day washout was outweighed by the extra burden placed on patients. All patients will be able to continue their standard medication throughout the duration of the study.

The safety, tolerability, and efficacy of ranolazine given in combination with standard CD treatments will be assessed as outlined in the following endpoints. The primary endpoint will be the mean change in daily number of loose stools. The secondary endpoints will be the mean change in Crohn's Disease Activity Index (CDAI) score, mean change in Short Inflammatory Bowel Disease Questionnaire (SIBDQ) score, mean change in Patient Health Questionnaire-9 (PHQ-9) score, and mean change in Harvey Bradshaw Index (HBI) score. The exploratory endpoint will be the time to 50% reduction in daily number of loose stools. The safety endpoint will be the rate of treatment emergent adverse effects.

Participant Selection

The primary recruitment strategy will be to recruit 20 patients directly from about 5000 patients that are currently seen at the Vanderbilt IBD Center. Throughout the enrollment period, a dedicated clinical research coordinator will review electronic health records (EHRs) of patients who have upcoming routine clinic visits to identify those who meet eligibility criteria. These patients will be flagged for recruitment and will be presented the study during a routine visit. Those who meet eligibility criteria will be enrolled in the study. Enrolled participants will complete clinical assessments, provide urine for pregnancy testing (limited to women of childbearing potential), and be randomized to their treatment sequence. Their next study visit will be scheduled, and they will be sent home with study medication.

Other recruitment methods may include MyResearchAtVanderbilt (MRAV), MRAV is a participant repository recruitment tool available to Vanderbilt researchers that reaches over 18,000 My Health at Vanderbilt users that have previously confirmed they would like to be contacted directly for research, including email. Further recruitment methods may include provider sponsored emails from the Principal Investigator to additional VUMC patients. Emails will be sent to VUMC patients not in MRAV, identified using Vanderbilt's Research Derivative (a database of clinical and related data derived from the Medical Center's clinical systems and restructured for research), who have 2 or more Crohn's Disease diagnostic codes, and an e-mail address within their EHR though the Data Coordinating Core (DCC). Both the MRAV email and the provider sponsored email will include links to a REDCap screening survey.

The study will include two distinct patient groups: Arm 1) CD in remission, defined as endoscopic or radiographic findings consistent with controlled CD in the past two years, but still experiencing symptoms (e.g., diarrhea, abdominal pain); Arm 2) Active CD, defined as endoscopic or radiographic findings consistent with active CD in the past two years. Inclusion criterion for a study participant will be to meet diagnostic criteria for CD with active diarrhea (≥3 loose stools per day on average). Exclusion criteria for a study participant will be the following: male and female subjects less than 18 years of age; significant change in medication including prednisone, antidepressant medications, or stimulants within the last 4 weeks (allowances include: Rectal hydrocortisone, rectal mesalamine, addition of prednisone (up to 20 mg) for flares, etc.); regular (daily) use of opioids or other drugs of abuse including heavy alcohol or marijuana use; severe psychiatric disease including schizophrenia, psychosis, suicidal depression; previous use of ranolazine within 2 months prior to enrollment; prior use of ranolazine which was discontinued for safety or tolerability; metabolic derangement defined as liver function tests >3× upper limit of normal or severe renal disease defined as calculated creatinine clearance <30 mL/min; have liver cirrhosis; concurrent use of strong CYP3A inhibitors or CYP3A inducers that may include: ketoconazole, clarithromycin, nelfinavir, rifampin, phenobarbital, or St. John's Wort; concurrent use of high dose simvastatin, Digoxine, TCA antidepressants or anti-psychotics, or metformin; concurrent use of OCT2 substrates; concurrent use of drugs transported by P-gp or drugs metabolized by CYP2D6; concurrent use of drugs known to prolong the QT interval; a family history of (or congenital) long QT syndrome or known acquired QT interval prolongation; inability or refusal to give informed consent for any reason including a diagnosis of dementia or cognitive impairment; patients who are pregnant or breastfeeding; patients who are enrolled in other investigational drug studies or who have taken investigational drugs within 30 days before enrollment; other factors which in the opinion of the investigator could potentially impact the study outcomes (e.g., underlying disease, medications, history) or prevent the participant from completing the protocol (poor compliance or unpredictable schedule). The study events are outlined in TABLE 4.

TABLE 4

| | Pre-Enrollment | Period 1 | | | Period 2 | |
|---|---|---|---|---|---|---|
| Procedure/ Assessment | Day −7-0 Prescreen patients with upcoming SOC appts | Day 0 Visit 1 Screen, enroll, randomize/ Period 1 baseline | Days 1-83 Daily text message and paper diary data collection | Crossover Day 84 Visit 2 Period 1 endpoint/ Period 2 baseline | Days 85-167 Daily text message and paper diary data collection | Day 168 Visit 3 Period 2 endpoint |
| EMR review | X | | | | | |
| Informed consent | | X | | | | |
| Medical history | | X | | X | | X |
| Physical exam including vital signs | | X | | X | | X |
| Concomitant meds | | X | | X | | X |
| Urine pregnancy test | | X | | X | | |
| Crohn's Disease Activity Index (CDAI) | | X | | X | | X |
| Short Inflammatory Bowel Disease Questionnaire (SIBDQ) | | X | | X | | X |
| Patient Health Questionnaire-9 (PHQ-9) | | X | | X | | X |
| Harvey Bradshaw Index (HBI) | | X | | X | | X |
| Randomization 1:1 | | X | | | | |
| Start study drug | | X | | X | | |
| Medication Diary | | X | X | X | X | X |
| Daily number of loose stools | | X | X | X | X | X |
| Adverse event monitoring | | X | X | X | X | X |

Procedure

Patients will be enrolled in the study for a total of 24 weeks. Patients entering the clinic for a routine visit will be recruited, consented, enrolled, and randomized at that same visit. They will undergo eligibility screening and be sent home with investigational medication. They will return at the end of the first 12-week study drug administration period for a mid-point study visit at which they will provide Period 1 endpoint/Period 2 baseline measurements and crossover to the second study drug administration period. As during the first administration period, they will return for the third and final study visit at the end of the second 12-week study drug administration period (Week 24/Day 168).

Participants will be allocated to treatment sequence (ranolazine first/placebo second or vice versa) using a block randomization module in REDCap. Equal numbers of participants will be randomized to the ranolazine-first and placebo-first groups. Participants will also be stratified based on remission status so that equal numbers of participants are enrolled in Arms 1 and 2. The investigator will instruct all patients to take the study drug exactly as specified in the protocol. A medication diary will be given to all patients enrolled in the study. Ranolazine and placebo will be dispensed as 500 mg tablets and encapsulated. The full dose will be 500 mg twice per day (BID). Patients will be given a sufficient number of capsules to last until the next visit. All patients will take ranolazine and placebo, each for 12 weeks. This study drug administration protocol is outlined in FIG. 1.

Study drugs will be taken at approximately the same time each day, such as in the morning and evening, and no earlier than 1 hour and no later than 4 hours after the scheduled time. Each dose of ranolazine will be taken with a glass of water. Ranolazine may be dosed with or without food. Ranolazine capsules should never be chewed, cut, or crushed. The entire contents of the ranolazine capsules will be consumed; the dose will not be divided. If a dose is missed (i.e., not taken within 4 hours after the scheduled dosing time), the patient will resume dosing with the next scheduled dose. Missed or vomited doses will not be made up. These events will be noted in the medication diary. Patients will be asked to record the time and date they take each dose in the medication diary. Patients will also be given instructions for self-administration as to the number and strength of the capsules to take. Urine will be collected from female participants of childbearing potential during study visits 1-2 for a urine pregnancy test.

Efficacy Assessment

CDAI, considered the 'gold standard' for defining clinical endpoints in CD trials, is an assessment predominantly used in research settings to quantify CD symptoms. The CDAI is a composite score ranging from 0 to approximately 600, with higher scores indicating greater disease activity. The 8 components used to assess the CDAI and their weighting factors are noted in TABLE 5.

TABLE 5

| Clinical or Laboratory Variable | Weighting |
|---|---|
| Number of liquid or soft stools each day for 7 days | ×2 |
| Abdominal pain (graded 0-3 on severity) each day for 7 days | ×5 |
| General well-being, from 0 (well) to 4 (terrible) daily for 7 days | ×7 |
| Presence of extraintestinal complications | ×20 |
| Taking diphenoxylate/atropine, loperamide, or opiates for diarrhea | ×30 |
| Presence of an abdominal mass (0 as none, 2 as questionable, 5 as definite) | ×10 |
| Hematocrit of <0.47 In men and <0.42 in women | ×6 |
| % deviation from standard weight | ×1 |

Clinical remission based on CDAI score is defined as a CDAI score of <150. Clinical response is defined as CDAI reduction from baseline of ≥100 points or CDAI score <150. Clinical remission based on abdominal pain and stool frequency is defined as an average stool frequency score ≤3 with a stool frequency no worse than baseline and an average abdominal pain score ≤1. MyCap will be used to collect the daily number of loose stools and antidiarrheal use from all subjects. MyCap is a secure mobile application developed within the REDCap environment, a web-based software providing secure and customizable approaches for data collection (Harris et al., *J Biomed Inform.* 2009 42 (2), 377-381). MyCap is equipped for periodic collection of patient-reported outcomes by brief survey within the application installed on their personal device.

The following questionnaires and index also will be used to assess the efficacy of the study drug. The SIBDQ is a 10-item shortened version of the original 32-item Inflammatory Bowel Disease Questionnaire (IBDQ). The SIBDQ measures quality of life in four domains: bowel symptoms, emotional health, systemic symptoms, and social function (Irvine et al., *Am J Gastroenterol.* 1996 91 (8), 1571-1578). The PHQ-9 is a 9-item module that screens for the presence and severity of depression and can be used to make a depression diagnosis using DSM-IV criteria (Kroenke et al., *J Gen Intern Med.* 2001 16 (9), 606-613). The HBI was conceived in 1980 as a simplified version of the CDAI to foster a systematic collection of clinical data related to Crohn's disease. The index considers five parameters, exclusively clinical (patient well-being, abdominal pain, number of liquid or soft stools, abdominal mass, complications). For each parameter a specific score is assigned (Harvey and Bradshaw, *Lancet Lond Engl.* 1980 1 (8167), 514).

Description of Study Drug

The study drug, 500 mg extended release generic ranolazine tablets, will be obtained by Vanderbilt's Investigational Drug Service (IDS). IDS will over-encapsulate ranolazine tablets at the IDS pharmacy. The tablet will be covered with microcrystalline cellulose in the capsule. The matching placebo manufactured for this study will be identical in appearance and will also be compounded at IDS. Ranolazine and placebo can be stored at room temperature for up to 12 months. Overall study noncompliance is defined as taking less than 80% or more than 120% of study drug during each treatment period. Subjects exhibiting poor compliance, i.e. 2 or more missed medication days in 1 week, as assessed by medication counts and review of the medication diary at each visit, will be counseled on the importance of good compliance to the study dosing regimen. Subjects who are persistently noncompliant (<80% or >120%) may be removed from the study.

Any medication that is considered necessary for the subject's health and is not expected to interfere with the evaluation of or interact with ranolazine may be continued during the study. All patients must remain on a stable dose of their standard CD medications throughout the course of the study. Use of antidiarrheals such as loperamide is permitted and will be tracked.

Statistical Analyses

The following analysis populations will be used in the statistical analysis. Intent-to-treat (ITT), the ITT analysis population will consist of all randomized subjects from the screened analysis population who receive at least one dose of study medication. Outcomes for the subjects in the ITT analysis population will be analyzed according to actual treatment received during the study drug administration period when the outcome measure was collected. The primary analysis population for all efficacy endpoints will be the ITT analysis population. Safety, the safety analysis population is defined as all subjects who are randomized and receive at least one dose of study medication, analyzed by actual treatment received. Per-protocol (PP), the PP population will consist of all patients in the ITT population who adhere to the protocol. This population will be used in sensitivity analyses of the primary and key secondary endpoints to evaluate the influence of major protocol violators and protocol deviators on the primary results.

Differences in the average effect of treatment for each proposed outcome will be tested for using separate paired t-tests. For subjects randomized to receive ranolazine first, the response at the end of Period 1 (Visit 2) to the response at the end of Period 2 (Visit 3) will be compared; for subjects randomized to receive placebo first, Visit 3 to Visit 2 will be compared. Results will be expressed as the mean effect of treatment with corresponding 95% confidence intervals. Semi-parametric approaches will be used to adjust for multiple comparisons among correlated hypotheses and anticipate that randomization and the paired analysis approach will mitigate confounding.

Figure 2:
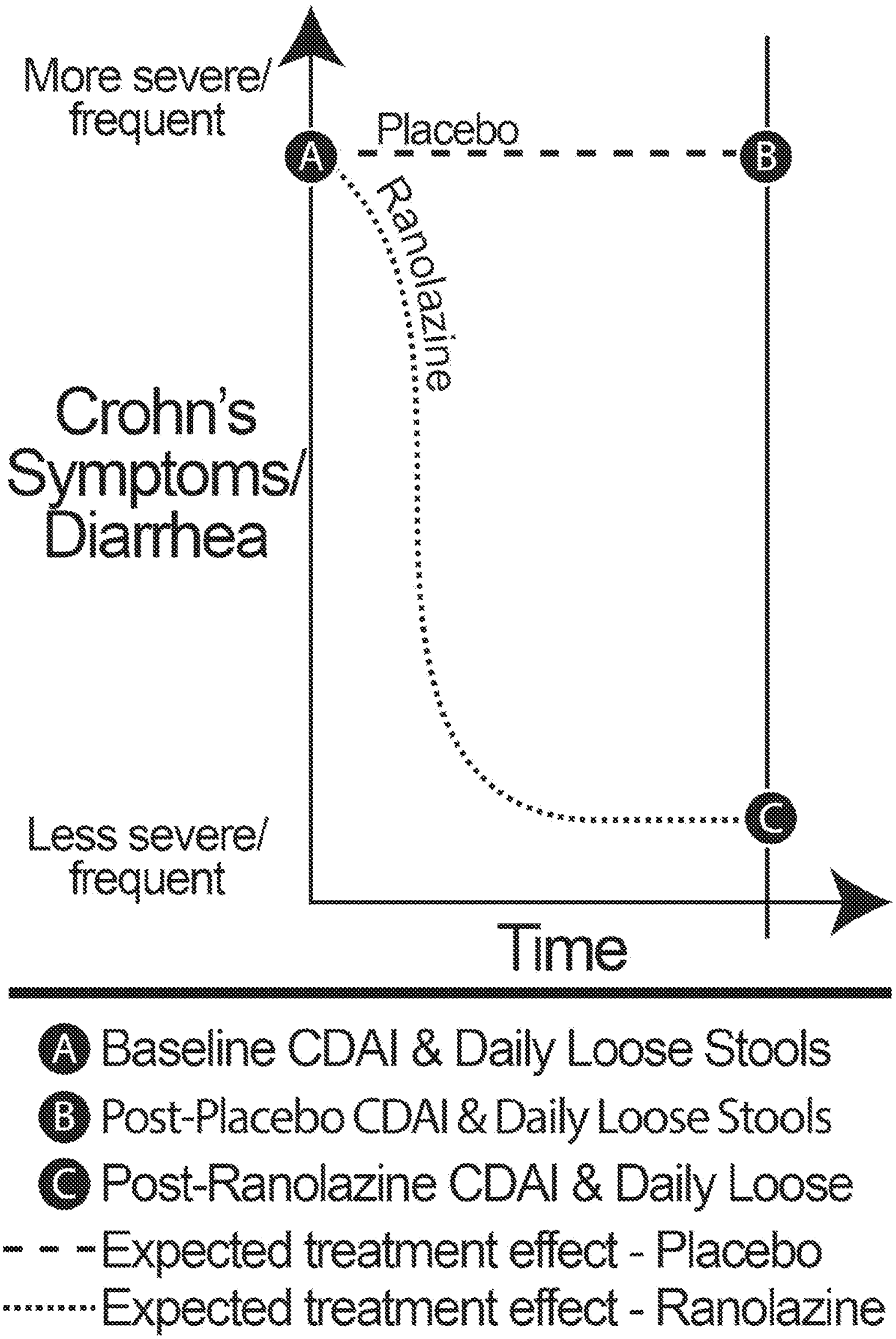
FIG. 2 shows the potential effect of ranolazine on CD symptoms.
Figure 3:
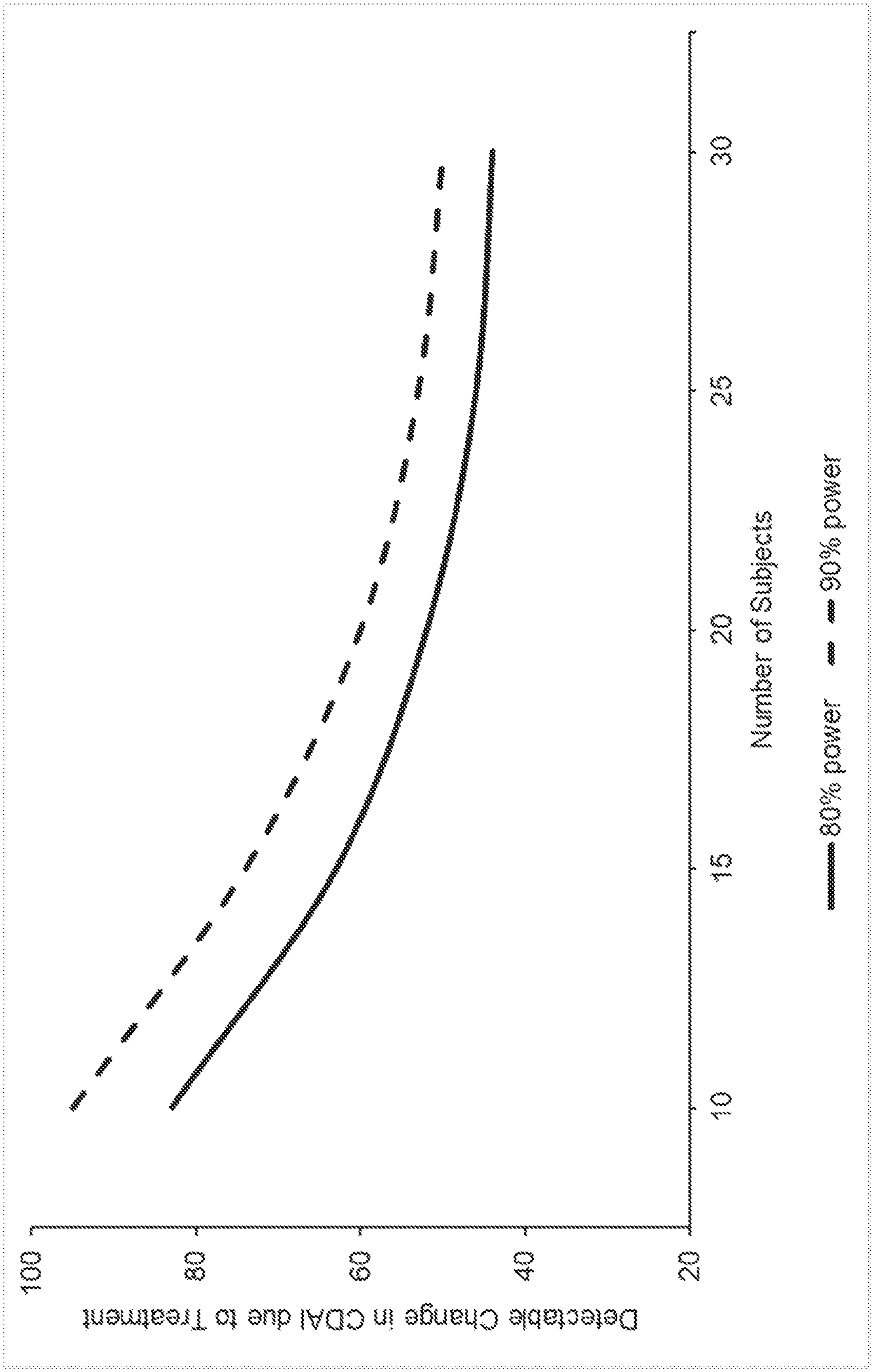
FIG. 3 shows power curves for detecting change in CDAI as a result of treatment.
Figure 4A:
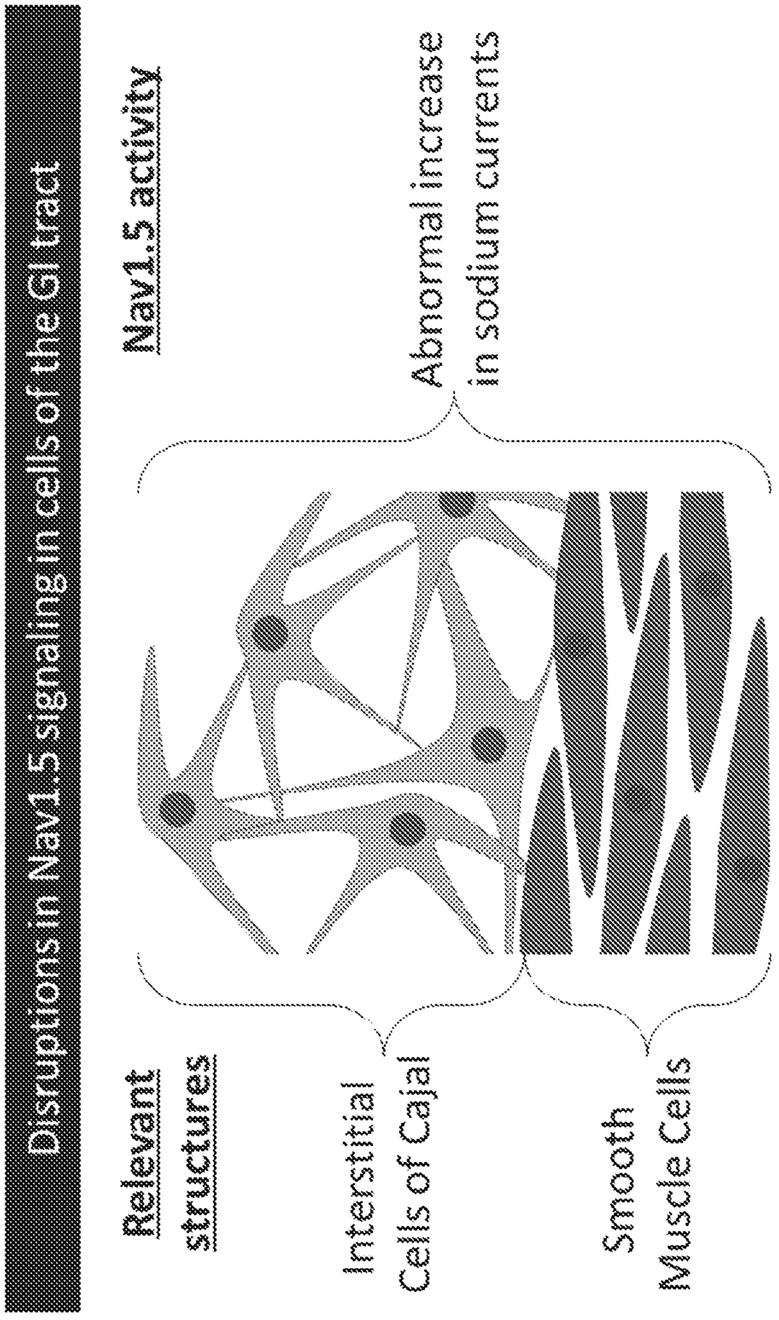
FIG. 4A-B show a hypothetical rendering of a gut dysmotility disorder as it relates to sodium channel protein type 5 subunit alpha (Nav1.5), a target of ranolazine.
Figure 4B:
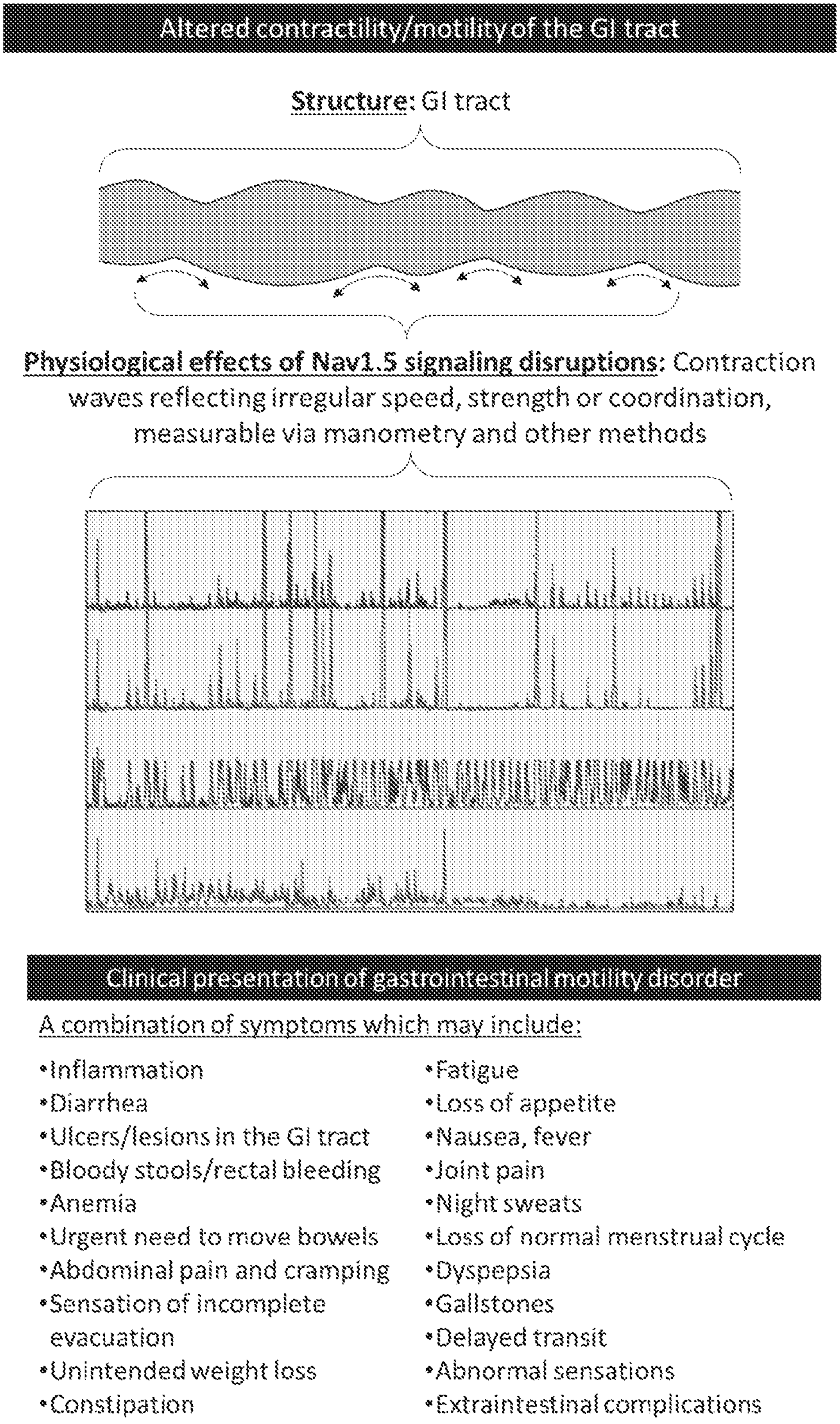

To utilize the longitudinal data collected at multiple visits and test hypotheses related to the timing of treatment effectiveness, the paired t-test will be generalized to a regression model framework. Separate longitudinal regression models will be estimated that include fixed effects of time, treatment-group indicator, and the time by treatment indicator interaction. To account for correlation arising from taking repeated measurements on the same subject over time, either random effects (continuous outcomes) or generalized estimating equations with the robust Huber-White sandwich estimator clustering on subject identifier (binary, ordinal, count outcomes) will be used. For outcomes measured at visits 1-3, time will be modeled as a factor (categorical) variables, and for diary data collected daily, time will be flexibly modeled using regression splines. These models will allow for estimation of the changing effect of treatment over time. The regression model can also be modified to test secondary hypotheses about dose effects (500 mg versus 1000 mg) by replacing the treatment indicator with dose received. The diary data will be used to evaluate compliance and model changes in the number of stools per day over time. While the primary analysis will be intent to treat, secondary analyses will be considered to determine if rate of compliance modifies the effect of treatment. For the number of stools per day analysis, a Poisson longitudinal regression model will allow for estimation of the quantities described in FIG. 2 including to time to symptom reduction and time to symptom recurrence after treatment discontinuation.

Power and sample size: 16 total subjects (8 in each arm) will be enrolled. Previously published (Irvine et al., *Am J Gastroenterol.* 1996 91 (8), 1571-1578) and preliminary data collected at Vanderbilt were used to estimate the standard deviation of the difference based on the standard deviation of the outcome and intraclass correlation. Accounting for multiple comparisons at a significance level of 0.05, there will be 80% power to detect changes of 63, 9.4, and 4.1 points for the CDAI, SIBDQ, and PHQ-9 outcomes. Using a rate of 3 loose stools per day, there will be 80% power to detect a reduction of 1.05 stools per day, or 7.35 per week (primary endpoint).

Adverse Events

Adverse events (AEs) include any of the following: worsening (change in nature, severity or frequency) of conditions present at the onset of the trial, subject deterioration due to the primary illness, intercurrent illnesses, drug interactions, events related or possibly related to concomitant medications, abnormal laboratory values or changes of vital signs, as well as significant shifts from baseline within the range of normal, which the Investigator considers to be clinically significant. CD relapse and related symptoms will be monitored as study endpoints and thus will not be recorded as AEs. In cases of surgical or diagnostic procedures, the condition/illness leading to such a procedure is considered the AE rather than the procedure itself. Abuse, withdrawal, sensitivity or toxicity to a study drug will be reported as an AE. Overdose, accidental or intentional, that are associated with an AE will be reported on the electronic case report form (eCRF). Any sequela of an accidental or intentional overdose of a study drug will be reported as a serious adverse event (SAE) on the AE eCRF. The overdose resulting from in the SAE will be identified as the cause of the event on the SAE Report Form and eCRF but will not be reported as an SAE itself.

During clinical investigations, SAEs may occur. If the event is suspected to be drug-related, the event may be significant enough to lead to important changes in the way the medicinal product is developed (e.g., change in dose, population, needed monitoring, consent forms). This is particularly true for reactions, which, in their most severe forms, threaten life or function. A SAE or serious adverse drug experience (SADE) is any untoward medical occurrence that results in death, is life-threatening ("life-threatening" refers to an event in which the subject is at risk of death at the time of the event; it does not refer to an event which hypothetically might have caused death if it were more severe), requires inpatient hospitalization or prolongation of existing hospitalization, results in persistent or significant disability/incapacity (as per reporter's opinion), is a congenital anomaly/birth defect, is another medically important condition. Important medical conditions that may not result in death, be life-threatening or require hospitalization may be considered as SAEs or SADEs when, based upon appropriate medical judgment, they may jeopardize the subject or may require intervention to prevent one of the outcomes listed in the definition above. Examples of such events are intensive treatment in an emergency room or at home for allergic bronchospasm; blood dyscrasias or convulsions that do not result in hospitalization; or development of drug dependency or drug abuse (Code of Federal Regulations Title 21, Volume 5, 21CFR312.32, revised Apr. 1, 2006).

The Principal Investigator will determine the relationship of each SAE to study drug (i.e., causality) by using the classification criteria 'not related', 'possibly related', or 'probably related'. Descriptions of the three classification categories are as follows. Not related (must include at least the first two features): it does not follow a reasonable temporal sequence from administration of the drug; it could readily have been produced by the subject's clinical state, environmental or toxic factors, or other modes of therapy administered to the subject; it does not follow a known pattern to the suspected drug; it does not reappear or worsen when the drug is re-administered. Possibly related (must include at least the first two features): it follows a reasonable temporal sequence from administration of the drug; it could readily have been produced by the subject's clinical state, environmental or toxic factors, or other modes of therapy administered to the subject; it follows a known response pattern to the suspected drug. Probably related (must include at least the first 3 features): it follows a reasonable temporal sequence from administration of the drug; it could not be reasonably explained by the known characteristics of the subject's clinical state, environmental or toxic factors, or other modes of therapy administered to the subject; it disappears or decreases on cessation or reduction of dose. there are exceptions when an AE does not disappear upon discontinuation of the drug (e.g., bone marrow depression, fixed drug eruptions, tardive dyskinesia); it follows a known pattern of response to the suspected drug. Related (must include all of the following features): it follows a reasonable temporal sequence from administration of the drug; it could not be reasonably explained by the known characteristics of the subject's clinical state, environmental or toxic factors, or other modes of therapy administered to the subject; it disappears or decreases on cessation or reduction of dose, there are exceptions when an AE does not disappear upon discontinuation of the drug (e.g., bone marrow depression, fixed drug eruptions, tardive dyskinesia; it follows a known pattern of response to the suspected drug; it reappears or worsens if the drug is re-administered.

In the pre-approval clinical experience with a new medicinal product or its new usage, particularly as the therapeutic dose(s) may not be established, an adverse drug reaction is defined as: All noxious and unintended responses to a medicinal product related to any dose should be considered adverse drug reactions (ADR). An unexpected ADR is: An adverse drug reaction, the nature or severity of which is not consistent with the applicable product information, also known as reference safety information. The reference safety information is the package insert. SAEs related to the use of the study drug (ranolazine) are not expected to occur based on extensive previous human experience. Since ranolazine is a marketed drug with a well-established safety profile, non-serious adverse events will not be subject to expedited reporting for this study. For both AEs and SAEs, the Principal Investigator will provide a record of the start and stop dates of the event, the action taken with study drug as a result of an AE or SAE as applicable (e.g., discontinuation, interruption, or dose reduction of study drug, as appropriate), whether any concomitant and/or additional treatments were given for the event, and the outcome of the event. All SAEs that have not resolved upon discontinuation of the subject's participation in the study must be followed until recovered (returned to baseline), recovered with sequelae, or death (due to the SAE).

Pregnancy in itself is not regarded as an AE unless there is suspicion that the study drug may have interfered with the effectiveness of a contraceptive medication. Pregnancies or suspected pregnancies, i.e. positive pregnancy test in a female subject of childbearing potential regardless of disease state, occurring while the subject is on study drug, or within 30 to 45 days of the subject's last dose of study drug, are considered immediately reportable events. Study drug will be discontinued immediately.

Participants will be removed from study treatment when any of the following criteria applies. The reasons for discontinuation of protocol treatment include, but are not limited to: non-compliance with the study protocol, including, but not limited to not attending the scheduled visits (these patients will still be included in the overall evaluation of safety); unacceptable major toxicity (these patients will still be included in the overall evaluation of safety); intercurrent illness or condition that would, in the judgment of the treating investigator, affect assessment of clinical status to a significant degree or require discontinuation of study treatment; at subject's own request (these patients will be included in the overall evaluation of safety and response if the full protocol therapy was administered prior to withdrawal); study is closed for any reason (e.g. new information shows that the patient's welfare would be at risk if they continued study treatment); general or specific changes in the participant's condition render the participant unacceptable for further treatment in the opinion of the treating investigator. Subjects may voluntarily withdraw from the study at any time. No study data from patients who withdraw consent at any time will be used in analysis.

The study intends that patients will complete the full 24 weeks of study drug administration. If a patient discontinues study treatment for reasons clearly not related to study treatment, after completing fewer than the full 24-week course of study drug, then that patient will be considered not evaluable for efficacy analysis (will still be included in the safety analysis though) and may be replaced with a new patient.

The criteria for enrollment are to be followed explicitly. Reasons for discontinuation include, but are not limited to, the following: physician decision, the Principal Investigator must discontinue study drug if is determined that it is not safe or in the subject's best interest to receive further treatment; noncompliance with study drug, a subject may be discontinued from the study for failure to comply with the dosing regimen as specified by the protocol; noncompliance with protocol/protocol deviation, a subject fails to follow protocol procedures, or other event or decision that stands in contrast to the guidelines set in the protocol; adverse event, a subject must be discontinued from study drug if, in the judgment of the Principal Investigator or if specified in the protocol, the subject develops an AE such as an intercurrent illness or complication that justifies discontinuation from study drug.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the disclosure are set out in the following numbered clauses:

Clause 1. A method for treating a gastrointestinal motility disorder or reducing symptoms thereof in a subject in need thereof, the method comprising administering to the subject a therapeutically effective amount of a compound of Formula I:

(I)

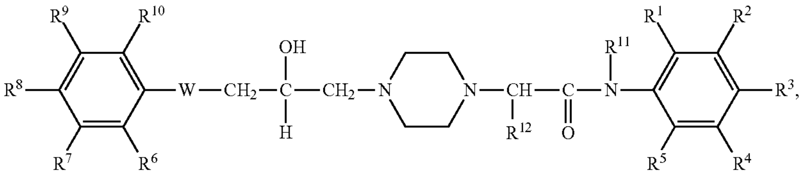

or a pharmaceutically acceptable ester or salt thereof, wherein: R1, R2, R3, R4 and R5 are each independently hydrogen, lower alkyl, lower alkoxy, cyano, trifluoromethyl, halo, lower alkylthio, lower alkyl sulfinyl, lower alkyl sulfonyl, or N-optionally substituted alkylamido (except that when R1 is methyl, R4 is not methyl); or R2 and R3 taken together form —OCHO2O—; R6, R7, R8, R9 and R10 are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, di (lower alkyl) amino; or R6 and R7 together form —CH═CH—CH═CH—; or R7 and R8 together form —OCH2O—; R11 and R12 are each independently hydrogen or lower alkyl; and Wis oxygen or sulfur; and, wherein the compound decreases contractility of gastrointestinal tract muscles.

Clause 2. The method of clause 1, wherein the compound is administered in the form of a composition wherein the composition comprises a pharmaceutically acceptable carrier.

Clause 3. The method of any one of the preceding clauses, wherein the compound is a compound of Formula II:

(II)

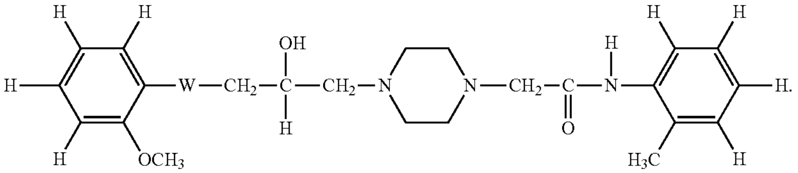

Clause 4. The method of any one of the preceding clauses comprising administering the pharmaceutically acceptable salt of the compound.

Clause 5. The method of any one of the proceeding clauses, wherein the gastrointestinal motility disorder is associated with Crohn's Disease.

Clause 6. The method of any one of the preceding clauses, wherein the compound is administered orally.

Clause 7. The method of any one of clauses 2-6, wherein the composition comprises about 500 mg to about 1000 mg of the compound.

Clause 8. The method of any one of clauses 2-7, wherein a daily dosage is about 2000 mg of the compound.

Clause 9. The method of any one of clauses 2-7, wherein a daily dosage is about 1000 mg of the compound.

Clause 10. The method of any one of clauses 2-7, wherein the composition comprises about 1000 mg of the compound.

Clause 11. The method of any one of clauses 2-7, wherein the composition comprises about 500 mg of the compound.

Clause 12. The method of any one of the preceding clauses, wherein the compound is administered to the subject more than once per day.

Clause 13. The method of any one of the preceding clauses, wherein the compound is administered about 6 hours to about 12 hours apart.

Clause 14. The method of any one of the preceding clauses, wherein the compound is administered once in the morning and the compound is administered once in the evening.

Clause 15. The method of any one of the preceding clauses, wherein following administration of the compound to the subject, abdominal pain is reduced.

Clause 16. The method of any one of the preceding clauses, wherein following administration of the compound to the subject, emotional disorders in the subject are reduced.

Clause 17. The method of clause 16, wherein the emotional disorders comprise anxiety, depression, anhedonia, antisocial disorder, agoraphobia, or combinations thereof.

Clause 18. The method of any one of the preceding clauses, wherein following administration of the compound to the subject, Crohn's disease symptoms in the subject are reduced.

Clause 19. The method of clause 18, wherein the Crohn's disease symptoms comprise diarrhea, fever, fatigue, abdominal pain, abdominal cramping, blood in stool, mouth sores, reduced appetite, weight loss, pain near or around the anus, drainage near or around the anus, fistulas, bloating, bowel obstruction, nausea, vomiting, flatulence, or a combination thereof.

Clause 20. The method of any one of the preceding clauses, wherein administration of the compound results in inhibition of a late sodium current of an action potential in gastrointestinal system cells.

Clause 21. The method of any one of the preceding clauses, wherein intracellular sodium is reduced in gastrointestinal system cells.

Clause 22. The method of clause 20 or clause 21, wherein intracellular calcium is reduced in the gastrointestinal system cells.

Clause 23. The method of any one of the preceding clauses, wherein intracellular ion homeostasis of gastrointestinal system cells is restored.

Clause 24. The method of any one of clauses 20-23, wherein the gastrointestinal system cells comprise intestinal smooth muscle cells (SMCs), motor neurons, sensory neurons, fibroblasts, interstitial cells of Cajal (ICC), epithelial cells, goblet cells, or combinations thereof.

Clause 25. The method of any one of the preceding clauses, wherein the compound is administered without food and at least 30 minutes prior to food consumption.

Clause 26. The method of any one of the preceding clauses, wherein the subject has active Crohn's disease.

Clause 27. The method of any one of the preceding clauses, wherein the subject has Crohn's disease that is in remission and exhibits diarrhea before administration of the compound.

Clause 28. The method of any one of the preceding clauses, wherein the subject exhibits ≥3 loose stools per day on average before administration of the compound.

Clause 29. The method of any one of the preceding clauses, wherein the compound is administered concomitantly with a secondary treatment for Crohn's disease.

Clause 30. The method of clause 29, wherein the secondary treatment for Crohn's disease comprises anti-inflammatories, immunosuppressants, antibiotics, analgesics, iron supplements, vitamin B-12 shots, calcium supplements, vitamin D supplements, or combinations thereof.

Clause 31. The method of clause 30, wherein the anti-inflammatories comprise corticosteroids, 5-aminosalicylates, or combinations thereof.

Clause 32. The method of clause 30, wherein the immunosuppressants comprise Azathioprine, Infliximab, Methotrexate, Natalizumab, Vedolizumab, Ustekinumab, or combinations thereof.

Clause 33. The method of any one of the preceding clauses, wherein the subject has a sodium voltage-gated channel alpha subunit 5 (SCN5A) channelopathy.

Clause 34. The method of clause 33, wherein the channelopathy increases sodium current.

Clause 35. The method of clause 33, wherein SCN5A is expressed in intestinal SMCs and/or ICC.

Clause 36. The method of any one of the preceding clauses, wherein the subject has uncoordinated temporal and spatial intestinal smooth muscle contractions and relaxations.

Clause 37. The method of any one of the preceding clauses, wherein temporal and spatial coordination of intestinal smooth muscle contractions and relaxations is restored following treatment.

Clause 38. The method of any one of the preceding clauses, wherein the subject is not constipated.

Clause 39. The method of any one of the preceding clauses, wherein the compound is ranolazine.

The invention claimed is:

1. A method for treating a gastrointestinal motility disorder or reducing symptoms thereof in a subject in need thereof, the method comprising administering to the subject a therapeutically effective amount of a compound of Formula I:

(I)

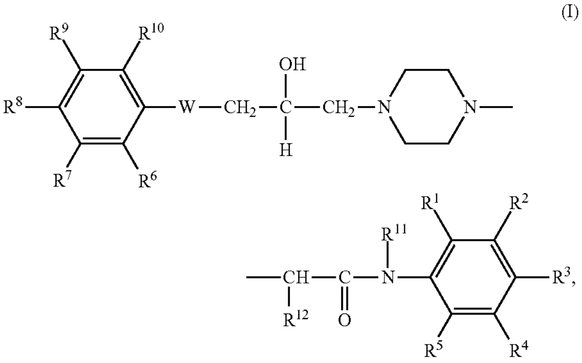

or a pharmaceutically acceptable ester or salt thereof, wherein:

$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido (except that when $R^1$ is methyl, $R^4$ is not methyl); or $R^2$ and $R^3$ taken together form $—OCHO_2O—$;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, di (lower alkyl) amino; or $R^6$ and $R^7$ together form $—CH{=}CH—CH—CH—$; or $R^7$ and $R^8$ together form $—OCH_2O—$;

$R^{11}$ and $R^{12}$ are each independently hydrogen or lower alkyl; and

W is oxygen or sulfur; and, wherein the compound decreases contractility of gastrointestinal tract muscles.

2. The method of claim 1, wherein the compound is administered in the form of a composition wherein the composition comprises a pharmaceutically acceptable carrier.

3. The method of claim 1, wherein the compound is a compound of Formula II:

(II)

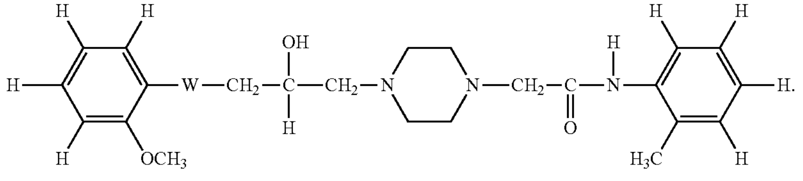

4. The method of claim 1, comprising administering the pharmaceutically acceptable salt of the compound.

5. The method of claim 1, wherein the gastrointestinal motility disorder is associated with Crohn's Disease.

6. The method of claim 1, wherein the compound is administered orally.

7. The method of claim 2, wherein the composition comprises about 500 mg to about 1000 mg of the compound.

8. The method of claim 2, wherein a daily dosage is about 1000 to about 2000 mg of the compound.

9. The method of claim 1, wherein the compound is administered to the subject at least once per day.

10. The method of claim 1, wherein following administration of the compound to the subject, abdominal pain is reduced.

11. The method of claim 1, wherein following administration of the compound to the subject, emotional disorders comprising anxiety, depression, anhedonia, antisocial disorder, agoraphobia, or combinations thereof in the subject are reduced.

12. The method of claim 1, wherein following administration of the compound to the subject, Crohn's disease symptoms comprising diarrhea, fever, fatigue, abdominal pain, abdominal cramping, blood in stool, mouth sores, reduced appetite, weight loss, pain near or around the anus, drainage near or around the anus, fistulas, bloating, bowel obstruction, nausea, vomiting, flatulence, or a combination thereof in the subject are reduced.

13. The method of claim 1, wherein administration of the compound results in inhibition of a late sodium current of an action potential in gastrointestinal system cells.

14. The method of claim 1, wherein intracellular ions are reduced and homeostasis is restored in gastrointestinal system cells.

15. The method of claim 1, wherein the subject has active Crohn's disease.

16. The method of claim 1, wherein the subject has Crohn's disease that is in remission and exhibits diarrhea before administration of the compound.

17. The method of claim 1, wherein the subject exhibits ≥3 loose stools per day on average before administration of the compound.

18. The method of claim 1, wherein the compound is administered concomitantly with a secondary treatment for Crohn's disease.

19. The method of claim 1, wherein the subject has a sodium voltage-gated channel alpha subunit 5 (SCN5A) channelopathy.

20. The method of claim 1, wherein the compound is ranolazine.

* * * * *